US008921568B2

(12) United States Patent
Kiappes et al.

(10) Patent No.: US 8,921,568 B2
(45) Date of Patent: Dec. 30, 2014

(54) IMINOSUGARS AND THEIR APPLICATIONS

(71) Applicants: Unither Virology, LLC, Washington, DC (US); The Chancellor, Masters and Scholars of the University of Oxford, Oxford (GB)

(72) Inventors: J. L. Kiappes, Oxford (GB); Peter Laing, Willingham (GB); Raymond Dwek, Oxfordshire (GB); Nicole Zitzmann, Oxfordshire (GB); Stephanie Pollock, Oxfordshire (GB)

(73) Assignees: Unither Virology, LLC, Silver Spring, MD (US); The Chancellor, Masters and Scholars of The University of Oxford, Oxford (GB)

( * ) Notice: Subject to any disclaimer, the term of this patent is extended or adjusted under 35 U.S.C. 154(b) by 0 days.

(21) Appl. No.: 13/910,564

(22) Filed: Jun. 5, 2013

(65) Prior Publication Data

US 2013/0331578 A1 Dec. 12, 2013

Related U.S. Application Data

(60) Provisional application No. 61/656,265, filed on Jun. 6, 2012.

(51) Int. Cl.
*C07D 401/12* (2006.01)
*C07D 211/46* (2006.01)

(Continued)

(52) U.S. Cl.
CPC ............ *C07D 405/12* (2013.01); *C07D 211/46* (2013.01); *C07D 401/12* (2013.01); *C07J 43/003* (2013.01)
USPC ........ 546/282.7; 546/196; 546/219; 514/337; 540/113; 540/200

(58) Field of Classification Search
USPC ........................................ 514/337; 546/282.7
See application file for complete search history.

(56) References Cited

U.S. PATENT DOCUMENTS 4,407,809 A * 10/1983 Junge et al. .................. 514/319
6,177,447 B1 1/2001 Aerts et al.

(Continued)

FOREIGN PATENT DOCUMENTS

JP 56103163 * 8/1981
WO WO 2004/047719 A2 6/2004

(Continued)

OTHER PUBLICATIONS

Aizaki et al., "Characterization of the hepatitis C virus RNA replication complex associated with lipid rafts," Virology, 2004, 324(2): 450-461.

(Continued)

*Primary Examiner* — John Mabry
*Assistant Examiner* — Daniel Carcanague
(74) *Attorney, Agent, or Firm* — Foley & Lardner LLP

(57) ABSTRACT

Iminosugar compounds are described that have inbuilt delivery features by virtue of covalent incorporation of a tocopherol moiety, or alternative moieties that are analogs of tocopherol or select analogs of cholesterol, or its antagonist "Ezitimibe"; and are likely to have broad spectrum antiviral activity. The compounds differ from previous iminosugar compounds, even lipophillic ones, being more hydrophobic and resembling fats and oils in their partition behavior in vivo into lipid phases of lipoproteins, cellular lipid droplet organelles and biological membranes. These features confer a number of unique delivery attributes in vivo, favorable to the therapy of virus infections involving cells of the lymphoid system and the liver, in particular, but these features are also favorable in general for the treatment of virus infections of man and animals.

17 Claims, 4 Drawing Sheets

Figure 1:
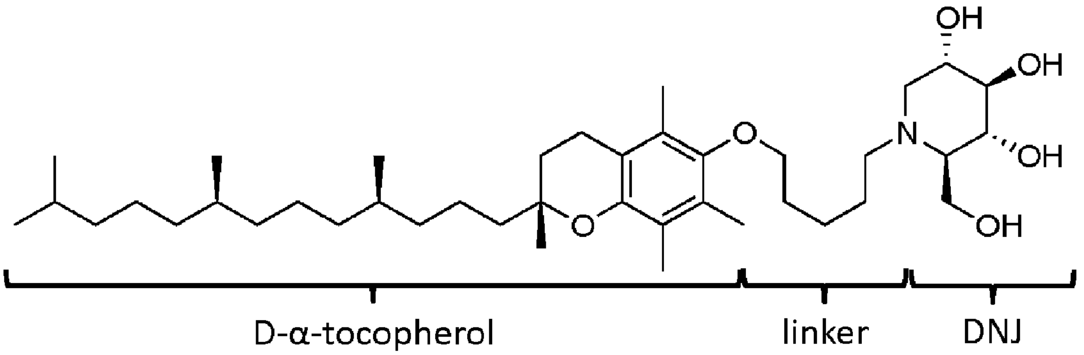

(51) Int. Cl.

| | |
|---|---|
| ***C07D 405/12*** | (2006.01) |
| ***A61K 31/575*** | (2006.01) |
| ***A61K 31/445*** | (2006.01) |
| ***A61P 31/12*** | (2006.01) |
| ***A61K 31/335*** | (2006.01) |
| ***C07J 43/00*** | (2006.01) |

(56) References Cited

U.S. PATENT DOCUMENTS

| | | | |
|---|---|---|---|
| 6,465,487 | B1 | 10/2002 | Block et al. |
| 6,465,488 | B1 | 10/2002 | Butters et al. |
| 6,545,021 | B1 | 4/2003 | Mueller et al. |
| 6,660,749 | B2 | 12/2003 | Butters et al. |
| 6,689,759 | B1 | 2/2004 | Jacob et al. |
| 6,809,083 | B1 | 10/2004 | Mueller et al. |
| 7,256,005 | B2 | 8/2007 | Zitzmann et al. |
| 7,312,232 | B2 | 12/2007 | Sanders et al. |
| 7,612,093 | B2 | 11/2009 | Jacob et al. |
| 7,816,560 | B1 | 10/2010 | Zitzmann et al. |
| 8,426,445 | B2 | 4/2013 | Ramstedt et al. |
| 8,450,345 | B2 | 5/2013 | Ramstedt et al. |
| 2003/0100532 | A1 | 5/2003 | Jacob et al. |
| 2003/0220299 | A1 | 11/2003 | Mueller et al. |
| 2005/0065150 | A1 | 3/2005 | Wang et al. |
| 2005/0267153 | A1 | 12/2005 | Mueller et al. |
| 2006/0106065 | A1 | 5/2006 | Jacob et al. |
| 2006/0264468 | A1 | 11/2006 | Mueller et al. |
| 2007/0275998 | A1 | 11/2007 | Butters et al. |
| 2008/0138351 | A1 | 6/2008 | Dwek et al. |
| 2009/0252785 | A1 | 10/2009 | Pollock et al. |
| 2010/0137365 | A1 | 6/2010 | Zitzmann et al. |
| 2010/0222384 | A1 | 9/2010 | Ramstedt et al. |
| 2010/0266678 | A1 | 10/2010 | Dwek et al. |
| 2011/0065752 | A1 | 3/2011 | Ramstedt et al. |
| 2011/0065753 | A1 | 3/2011 | Ramstedt et al. |
| 2011/0065754 | A1 | 3/2011 | Ramstedt et al. |
| 2011/0136868 | A1 | 6/2011 | Karadimitris et al. |
| 2011/0182982 | A1 | 7/2011 | Dwek et al. |
| 2011/0184019 | A1 | 7/2011 | Zitzmann et al. |
| 2012/0237592 | A1 | 9/2012 | Pollock et al. |
| 2013/0150405 | A1 | 6/2013 | Ramstedt et al. |
| 2013/0237567 | A1 | 9/2013 | Ramdstedt et al. |

FOREIGN PATENT DOCUMENTS

| | | | |
|---|---|---|---|
| WO | WO 2006/025687 | A1 | 3/2006 |
| WO | WO 2006/107936 | A1 | 10/2006 |
| WO | WO 2010/027996 | A1 | 3/2010 |

OTHER PUBLICATIONS

Aizaki et al., "Critical Role of Virion-Associated Cholesterol and Sphingolipid in Hepatitis C Virus Infection," J Virol., 2008, 82(12): 5715-5724.

Bavari et al., "Lipid Raft Microdomains: A Gateway for Compartmentalized Trafficking of Ebola and Marburg Viruses," J Exp Med., 2002, 195(5): 593-602.

Block et al., "Secretion of Human Hepatitis B Virus is Inhibited by the Imino Sugar N-Butyldeoxynojirimycin," PNAS USA, Mar. 1994, 91:2235-2239.

Campbell et al., "Virion-associated cholesterol is critical for the maintenance of HIV-1 structure and infectivity," AIDS, 2002, 16(17): 2253-2261.

Chapel et al., "Reduction of the infectivity of hepatitis C virus pseudoparticles by incorporation of misfolded glycoproteins induced by glucosidase inhibitors," J. Gen. Virol., 2007, 88:1133-1143.

Fischer et al., "The α-Glucosidase Inhibitor N-Butyldeoxynojirimycin Inhibits Human Immunodeficiency Virus Entry at the Level of Post-CD4 Binding," J. Virol, Sep. 1995, 69(9):5791-5797.

Guyader et al., "Role for Human Immunodeficiency Virus Type 1 Membrane Cholesterol in Viral Internalization," J Virol., 2002, 76(20): 10356-10364.

Jordan et al.. "Inhibition of Host ER Glucosidase Activity Prevents Golgi Processing of Virion-Associated Bovine Viral Diarrhea Virus E2 Glycoproteins and Reduces Infectivity of Secreted Virions," Virology, 2002, 295:10-19.

Leser et al., "Influenza virus assembly and budding in raft-derived microdomains: A quantitative analysis of the surface distribution of HA, NA and M2 proteins," Virology, 2005, 342(2): 215-227.

Leu et al., "Anti-HCV activities of selective polyunsaturated fatty acids," Biochem. Biophys. Res. Commun., 2004, 318:275-280.

Ono et al., "Plasma membrane rafts play a critical role in HIV-1 assembly and release," Proc Natl Acad Sci U S A., 2001, 98(24): 13925-13930.

Orsato A, "Iminosugar Analogues of Phosphatidyl Inositol as Potential Inhibitors of Protein Kinase B (Akt)," Eur. J. Org. Chem., Jul. 27, 2011, 26:5012-5019.

Pollock et al., "N-Butyldeoxynojirimycin is a broadly effective anti-HIV therapy significantly enhanced by targeted liposome delivery," AIDS, 2008, 22:1961-1969.

Popik et al., "CD4 Receptor Localized to Non-raft Membrane Microdomains Supports HIV-1 Entry," J Biol Chem., 2004, 279(1): 704-712.

Scheiffele et al., "Influenza Viruses Select Ordered Lipid Domains during Budding from the Plasma Membrane," J Biol Chem., 1999, 274(4): 2038-2044.

Tanaka et al., "Antiviral effects of glycosylation and glucose trimming inhibitors on human parainfluenza virus type 3," Antiviral Research, 2006, 72:1-9.

Vincent et al., "Measles Virus Assembly within Membrane Rafts," J Virol., 2000, 74(21): 9911-9915.

Wu et al., "Antiviral Effects of an Iminosugar Derivative on Flavivirus Infections," J. Virol., Apr. 2002, 76(8):3596-3604.

Bartoli et al., "tert-Butyl Ethers: Renaissance of an Alcohol Protecting Group. Facile Cleavage with Cerium(III) Chloride/Sodium Iodide," Adv. Synth. Catal., 2006, 348:905-910.

Satoh et al., "Synthesis and Physiological Activity of Novel Tocopheryl Glycosides," Chem. Pharm. Bull., 2001, 49(8):948-953.

Shimada et al., "Biodistribution of liposomes containing synthetic galactose-terminated diacylglyceryl-poly(ethyleneglycol)s," Biochimica et Biophysica Acta, 1997, 1326:329-341.

* cited by examiner

| Compound | X = |
|---|---|
| 7 | $(CH_2)_n$, n ≥ 2 |
| 8 | $(CH_2)_n$, n ≥ 2, with one or more O, N or S substitution at irregular intervals |
| 9 | $(CH_2CH_2OCH_2CH_2)_n$, n ≥ 1 |
| 10 | $(CH_2CH_2N(R)CH_2CH_2)_n$, n ≥ 1, R = H or alkyl |
| 11 | $(CH_2CH_2SCH_2CH_2)_n$, n ≥ 1 |

8a 9a (n = 1)

| Compound | R1 | R2 | R3 | Tocopherol |
| --- | --- | --- | --- | --- |
| 1 | Me | Me | Me | alpha |
| 12 | Me | H | Me | beta |
| 13 | H | Me | Me | gamma |
| 14 | H | H | Me | delta |

| Compound | R1 | R2 | R3 | Tocotrienol |
| --- | --- | --- | --- | --- |
| 15 | Me | Me | Me | alpha |
| 16 | Me | H | Me | beta |
| 17 | H | Me | Me | gamma |
| 18 | H | H | Me | delta |

19

20

21

22

23

IMINOSUGARS AND THEIR APPLICATIONS

CROSS-REFERENCE TO RELATED APPLICATIONS

This application claims priority from U.S. Provisional Application No. 61/656,265, filed Jun. 6, 2012, the contents of which are hereby incorporated by reference in their entirety into the present disclosure.

FIELD

The present application relates to novel iminosugars and their methods of making and use and in particular, to novel deoxynojimimycin based compounds and their methods of making and use. There remains a need for new types of antiviral iminosugars.

SUMMARY

In one embodiment, provides a compound represented by the Formula:

A-L-IS wherein A is a hydrophobic molecular delivery moiety, L is a linking moiety and IS is an iminosugar moiety or an analogue thereof. One embodiment is a compound having formula I:

(I)

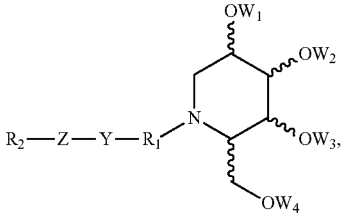

wherein:

$R_2$ is $C_2$-$C_6$ alkyl or oxaalkyl group; Y is O or $CH_2$; Z is selected from $(CH_2)_3$—O—$CH_2$; $(CH_2)_5$;

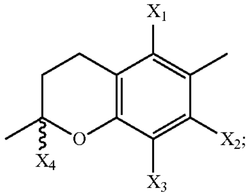

and

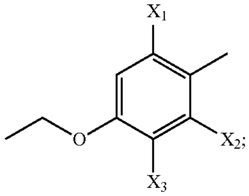

$R_2$ is a) straight or branched $C_{10}$-$C_{16}$ alkyl or alkylene groups and H, when Z is

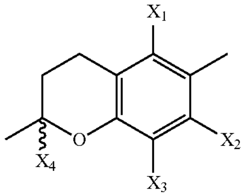

and b) straight or branched $C_{10}$-$C_{20}$ alkyl or alkylene groups, when Z is $(CH_2)_3$—O—$CH_2$; $(CH_2)_5$ or

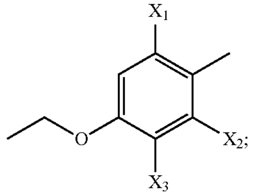

$W_{1-4}$ are each independently selected from H or an alcohol protecting group; and $X_{1-4}$ are each independently selected from H or $C_{1-2}$ alkyl. One embodiment is a compound of Formula I having formula II (II)

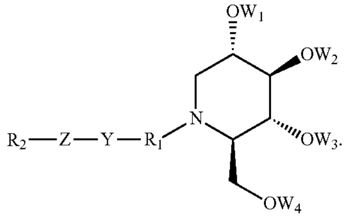

One embodiment is a compound of Formula I wherein $R_1$ is $C_5$ alkyl. One embodiment is a compound of Formula I, wherein —Z—Y— is

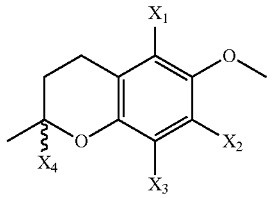

and wherein each of $X_{1-4}$ is independently selected from H or methyl. In one embodiment, $X_4$ is methyl and wherein $R_2$—Z—Y— is

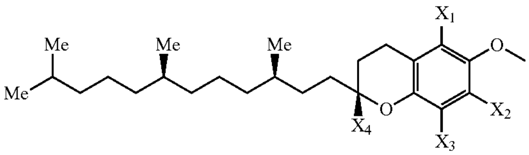

or

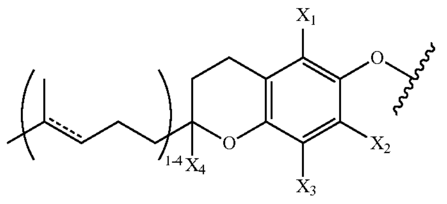

(wherein the methyl groups bonded to an sp3 carbon may each be R or S independently) or

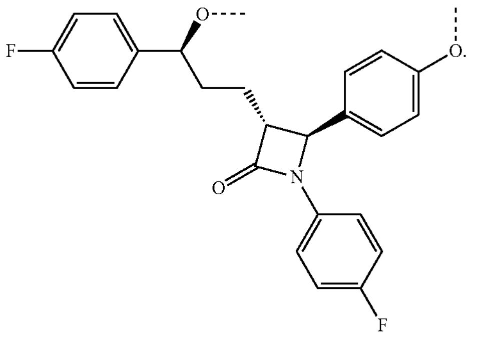

In another embodiment, $X_{1-4}$ are each methyl and $R_1$ is $C_5$ alky. In another embodiment, $W_{1-4}$ are each H. In another embodiment, $R_2$ is

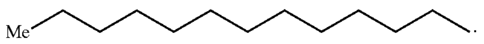

Another embodiment provides a method of making a compound of formula I (I)

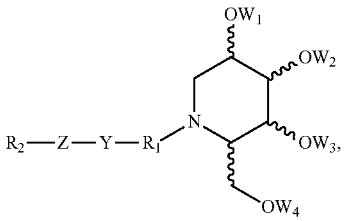

the method comprising: condensing a compound of formula III (III)

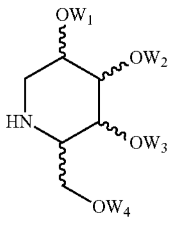

with a compound of formula IV (IV)

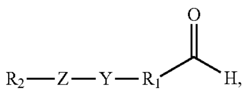

wherein: $R_1$ is $C_2$-$C_6$ alkyl or oxaalkyl group; Y is O or $CH_2$; Z is selected from $(CH_2)_3$—O—$CH_2$; $(CH_2)_5$;

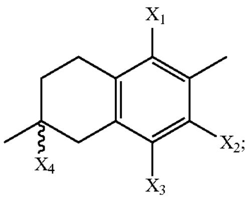

and

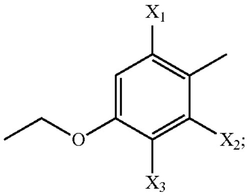

$R_1$ is a) straight or branched $C_{10}$-$C_{16}$ alkyl or alkylene groups and H, when Z is

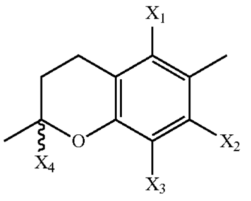

and b) straight or branched $C_{10}$-$C_{20}$ alkyl or alkylene groups, when Z is $(CH_2)_3$—O—$CH_2$; $(CH_2)_5$ or

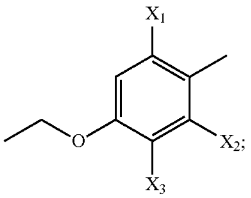

$W_{1-4}$ in the compound of formula I are each independently selected from H or alcohol protecting groups; $W_{1-4}$ in the compound of formula III are each independently selected from alcohol protecting groups; and $X_{1-4}$ are each independently selected from H or $C_{1-2}$ alkyl.

In one embodiment, the compound of formula I is

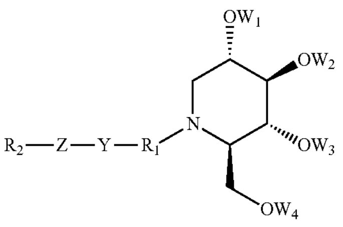

and the compound of formula III is

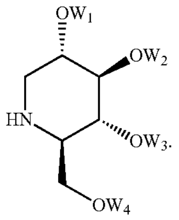

In one embodiment, Y is O.

In one embodiment, the method further comprises deprotecting a compound of formula V (V)

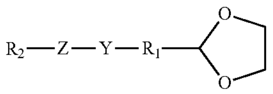

to form the compound of formula IV (IV)

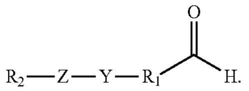

In one embodiment, the method further comprises reacting $R_2$—Z—OH with

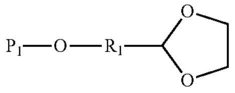

to form the compound of formula V (V)

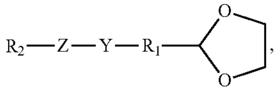

wherein $P_1$ is an alcohol protecting group.

In one embodiment, the method further comprises converting $R_2$—Z—Y—$R_1$—OH into the compound of formula IV (IV)

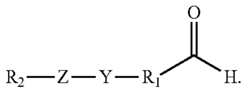

In one embodiment, the method further comprises deprotecting $R_2$—Z—Y—$R_1$—$OP_2$ to form $R_2$—Z—Y—$R_1$—OH, wherein $P_2$ is an alcohol protecting group. In one embodiment, the method further comprises reacting $R_2$—Z—OH with $P_3O$—$R_1$—$OP_2$ to form $R_2$—Z—Y—$R_1$—$OP_2$, wherein $P_3$ is an alcohol protecting group. In one embodiment, —Z—Y— is

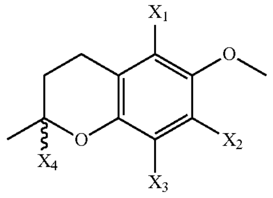

and wherein each of $X_{1-4}$ is independently selected from H or methyl.

Another embodiment provides a compound represented by formula XX'

XX'

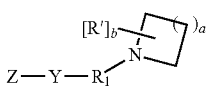

wherein:

$R_1$ is a linking moiety, preferably $(CH_2)_p$, optionally with one or more heteroatomic substitution or $(CH_2CH_2XCH_2CH_2)_q$;

p is an integer 2-20;

Y is a bond, $CH_2$, S, N(R), or O;

Z is a hydrophobic molecular delivery moiety described herein, preferably a tocopherol, tocotrienol, cholesterol, ezetimibe, or an analogue thereof;

a represents an integer from 1 to 7, provided that the ring may also contain at least one unsaturated C—C bond where n>1. b represents an integer from 1 to (a+2). y represents either 1 or 2, and z represents an integer from 1 to (y+7). R' represents OH; OR"; =O; $NH_2$; $N_3$; SH; $SO_xR$"; halo; CN; $NO_2$; NR"$R^3$; (NR")NR"$R^3$; NH(NR")NR"$R^3$; $CO_2R^3$; CONR"$R^3$; $NR^3$COR"; $NR^3SO_2$R"; P(O)(OR")$_2$; C1-15 alkyl or alkenyl optionally substituted with one or more OH, OR", =O, $NH_2$, $N_3$, SH, $SO_xR$", halo, CN, $NO_2$, NR"$R^3$, (NR")NR"$R^3$, NH(NR")NR"$R^3$, $CO_2R^3$, CONR"$R^3$, $NR^3$COR", $NR^3SO_2$R", P(O)(OR")$_2$, aryl or carbocyclyl groups; carbocyclyl or aryl, either of which is optionally substituted with one or more OH, OR", =O, $NH_2$, $N_3$, SH, $SO_xR^3$, halo, CN, $NO_2$, NR"$R^3$, (NR")NR"$R^3$, NH(NR")NR"$R^3$, $CO_2R^3$, CONR"$R^3$, $NR^3$COR", $NR^3SO_2$R", P(O)(OR")$_2$, C1-9 alkyl optionally substituted with one or more OH, OR", =O, $NH_2$, $N_3$, halo, CN, NO2, NR"$R^3$, $CO_2R^3$, CONR"$R^3$, aryl or carbocyclyl groups; O-glycosyl; C-glycosyl; O-sulfate; O-phosphate or a group which together with the endocyclic carbon forms a spiro ring, with the provisos that (a) two OH groups may not be attached to the same endocyclic carbon atom; (b) where there is only one R' substituent it contains an oxygen atom directly bonded to an endocyclic carbon atom; and (c) where b or z>1 any two R' substituents may together form an optionally heterocyclic ring (for example, a carbocycle, cyclic ether or acetal). R" represents H; C1-6 alkyl, optionally substituted with one or more OH; aryl or $C_{1-3}$ alkyl optionally substituted with aryl; $SiR^3{}_3$. $R^3$ represents H; C1-6 alkyl, optionally substituted with one or more OH. R" and $R^3$ may optionally form a 4 to 8 membered ring, containing one or more O, $SO_X$ or $NR^3$ groups. X represents an integer from 0 to 2 (inclusive).

In one embodiment, Z is

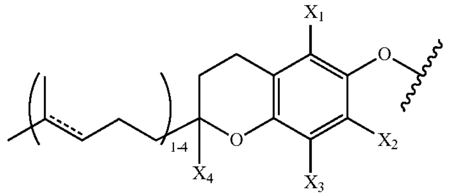

(wherein the methyl groups bonded to an sp3 carbon may each be R or S independently) wherein X1-4 are each methyl and R1 is C5 alkyl and the dashed line represents an optional double bond or wherein Z is

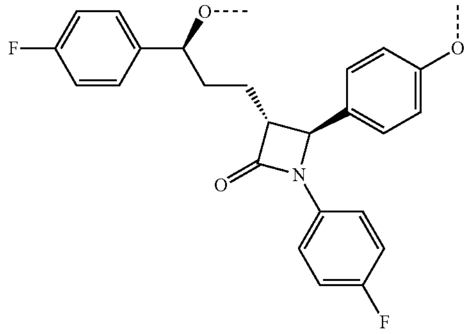

and at least one of the dashed lines represents a bond to the linker group or wherein Z is a cholesterol derivative or wherein Z is a diacylglyceryl derivative.

Another embodiment provides a compound of formula YY'

YY'

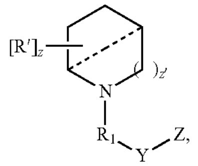

wherein:

$R_1$ is a linking moiety, preferably $(CH_2)_p$, optionally with one or more heteroatomic substitution or $(CH_2CH_2XCH_2CH_2)_q$; p is an integer 2-20 or q is an integer 1-10;

Y is a bond, $CH_2$, S, $N(R_3)$, or O;

Z is a hydrophobic molecular delivery moiety described herein, preferably a tocopherol, tocotrienol, cholesterol, ezetimibe, or an analogue thereof;

Z' represents 0 or an integer from 1 to 7, provided that the ring may also contain at least one unsaturated C—C bond; b represents an integer from 1 to (a+2). y represents either 1 or 2, and z represents an integer from 1 to (y+7). R' represents in each instance OH; OR"; =O; $NH_2$; $N_3$; SH; $SO_xR$"; halo; CN; $NO_2$; NR"$R^3$; (NR")NR"$R^3$; NH(NR")NR"$R^3$; $CO_2R^3$; CONR"$R^3$; $NR^3$COR"; $NR^3SO_2$R"; $P(O)(OR")_2$; C1-15 alkyl or alkenyl optionally substituted with one or more OH, OR", =O, $NH_2$, $N_3$, SH, $SO_xR$", halo, CN, $NO_2$, NR"$R^3$, (NR")NR"$R^3$, NH(NR")NR"$R^3$, $CO_2R^3$, CONR"$R^3$, $NR^3$COR", $NR^3SO_2$R", $P(O)(OR")_2$, aryl or carbocyclyl groups; carbocyclyl or aryl, either of which is optionally substituted with one or more OH, OR", =O, $NH_2$, $N_3$, SH, $SO_xR^3$, halo, CN, $NO_2$, NR"$R^3$, (NR")NR"$R^3$, NH(NR")NR"$R^3$, $CO_2R^3$, CONR"$R^3$, $NR^3$COR", $NR^3SO_2$R", $P(O)(OR")_2$, C1-9 alkyl optionally substituted with one or more OH, OR", =O, $NH_2$, $N_3$, halo, CN, NO2, NR"$R^3$, $CO_2R^3$, CONR"$R^3$, aryl or carbocyclyl groups; O-glycosyl; C-glycosyl; O-sulfate; O-phosphate or a group which together with the endocyclic carbon forms a spiro ring, with the provisos that (a) two OH groups may not be attached to the same endocyclic carbon atom; (b) where there is only one R' substituent it contains an oxygen atom directly bonded to an endocyclic carbon atom; and (c) where b or z>1 any two R' substituents may together form an optionally heterocyclic ring (for example, a carbocycle, cyclic ether or acetal). R" represents H; C1-6 alkyl, optionally substituted with one or more OH; aryl or $C_{1-3}$ alkyl optionally substituted with aryl; $SiR^3_3$. $R^3$ represents H; C1-6 alkyl, optionally substituted with one or more OH. R" and $R^3$ may optionally form a 4 to 8 membered ring, containing one or more O, $SO_x$ or $NR^3$ groups. X represents an integer from 0 to 2 (inclusive); the dotted line in structure YY represents an optional bridge containing 2 or 3 carbon atoms between any two different ring carbon atoms, any or all of which bridge or bridgehead carbon atoms being optionally substituted with R'.

In one embodiment, Z is

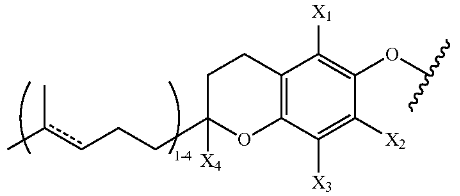

wherein X1-4 are each methyl and R1 is C5 alkyl and the dashed line represents an optional double bond.

In one embodiment, Z is

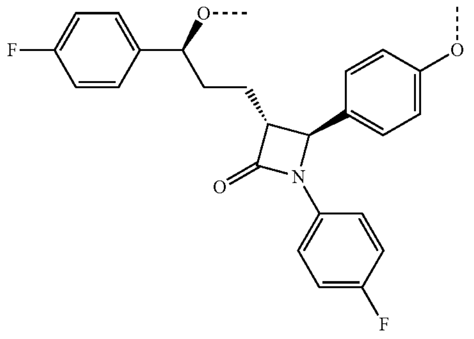

and at least one of the dashed lines represents a bond to the linker group.

In one embodiment, Z is a cholesterol derivative.

In one embodiment, Z is a diacylglyceryl derivative. In one embodiment, Z is Z"—$R_2$, wherein Z; is selected from $(CH_2)_3$—O—$CH_2$; $(CH_2)_5$;

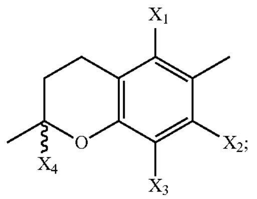

and

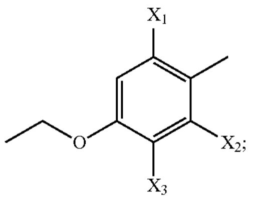

$R_2$ is a) a straight or branched $C_{10}$-$C_{16}$ alkyl or alkylene groups and H, when Z is

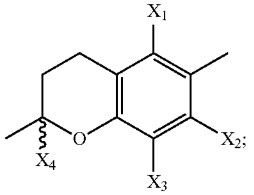

and b) a straight or branched $C_{10}$-$C_{20}$ alkyl or alkylene groups, when Z is $(CH_2)_3$—O—$CH_2$; $(CH_2)_5$ or

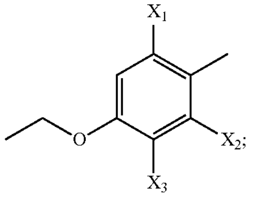

and $X_{1-4}$ are each independently selected from H or $C_{1-2}$ alkyl.

At least one aspect of one embodiment provides new methods of delivery of certain iminosugars or an analogue thereof. Further aspects of the present invention will become apparent from the disclosure that follows.

DRAWINGS

FIG. 1 shows an embodiment demonstrating the archetypal form of tocopheryl DNJ.

Figure 2:
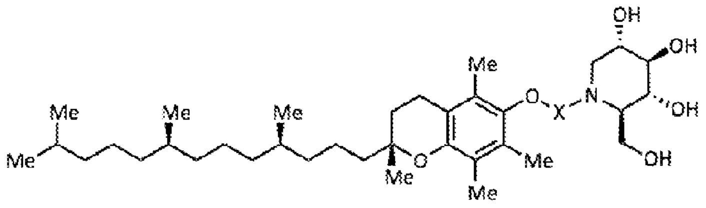

FIG. 2 shows an embodiment demonstrating various linker moieties embodied herein, as attached to the archetypal form of tocopheryl DNJ shown in FIG. 1. 7: The linker is composed entirely of methylene units, providing the most hydrophobic linker. Increasing chain length allows for greater flexibility meaning the iminosugar and chemophore will be less likely to interact. However, greater length also means a larger hydrophobic chain breaking up the hydrophilic iminosugar and phenolic oxygen. 8: Some of the hydrophobicity can be removed by introducing a heteroatom. In addition to interacting with water, if placed strategically, the atom may form an intramolecular hydrogen bond to the iminosugar or phenolic oxygen. (see FIG. 4). This can influence the pKa of the iminosugar nitrogen atom, as well as imposing novel 3-dimensional conformational preferences. 9, 10, and 11 include more than one heteroatom placed at regular intervals.

Figure 3:
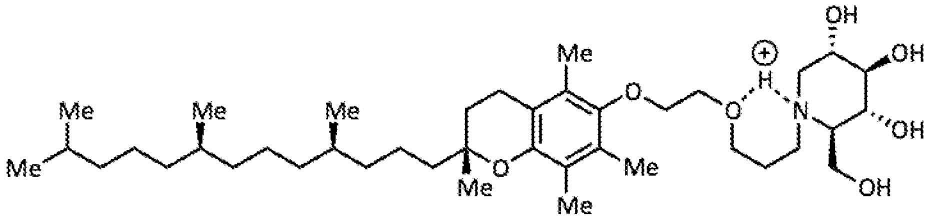
Figure 3:
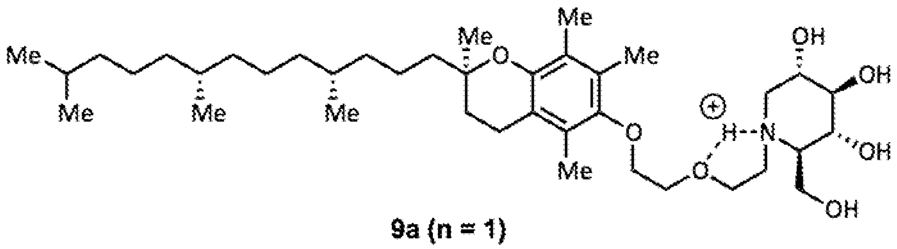

FIG. 3 shows an embodiment demonstrating representative structures of the intramolecular hydrogen bonds possible with heteroatom linkers. Both of these show linker-iminosugar hydrogen bonds, while linker-phenol and phenol-iminosugar hydrogen bonds are also possible. In order for these bonds to be energetically favorable, the hydrogen bond should be part of a 5-membered (as seen in 8a) or 6-membered (as seen in 9a) ring.

Figure 4:
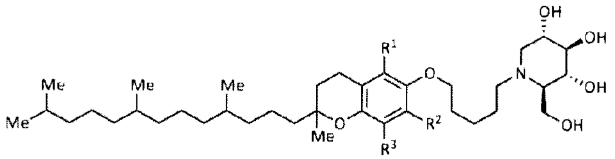
Figure 4:
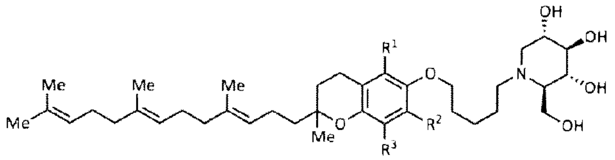
Figure 4:
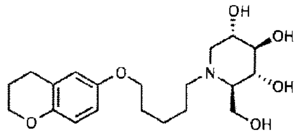
Figure 4:
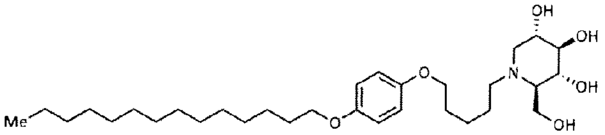
Figure 4:
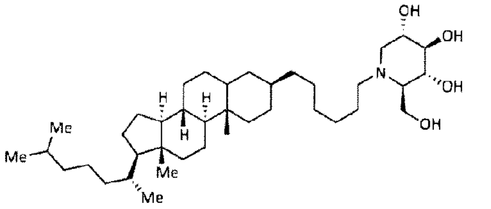
Figure 4:
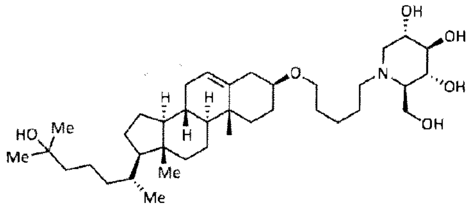
Figure 4:
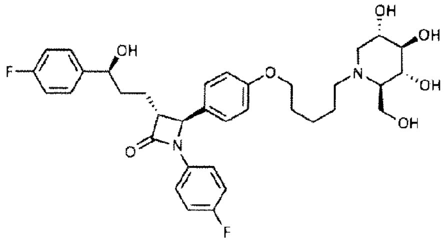

FIG. 4 shows various embodiments of chemophore analogues of tocopherol DNJ. Although the chemophores may be coupled with any linker and any iminosugar, in this figure, they are coupled with the archetypal DNJ and pentyl linker. 1: In addition to the R,R,R stereochemistry of the archetypal compound of the invention, the compounds with S stereochemistry at any or all of the 3 stereocenters are also being investigated. 12, 13, 14: By replacing 1 or 2 of the chromanol methyl groups with hydrogen atoms, the β-, γ-, and δ-tocopherol based iminosugars, respectively. 15-18: Rather than chiral methyl groups, the unsaturated tocotrienols are also viable lipids to be incorporated. 19 and 20 represent two simplified analogues of the archetypal iminosugar invention as part of a search for the minimum structural requirements for tocopherol mimicry. 21 and 22 show iminosugars where the tocopherol chemophore has been replaced with cholesterol analogues. In 21, the oxygen atom of cholesterol has been removed, while in 22 the analogue is 25-hydroxycholesterol. 23 shows one possible Ezitimibe analogue, though attachment of the linker at the secondary hydroxyl group is also possible.

DETAILED DESCRIPTION

Introduction

All references cited herein are incorporated by reference in their entirety.

Various inventions and/or their embodiments disclosed herein relate to compounds comprising at least one iminosugar moiety or analogue thereof, a linking moiety bonded to the amine in the at least one iminosugar moiety and at least one hydrophobic molecular delivery moiety bonded to the linker moiety. Other embodiments include compositions comprising at least one compound embodied herein, and methods of synthesizing the embodied compounds and compositions.

Important synthetic methods which can be used as appropriate herein to prepare compounds are generally known in the art and are described in, for example, *March's Advanced Organic Chemistry, 6th* Ed., 2007; T. W. Greene, *Protective Groups in Organic Synthesis*, John Wiley and Sons, 1991.

The term "or" as used herein means "and/or" unless specified other wise.

The term "a" or "an" as used herein means "at least one" unless specified other wise.

When referring to a moiety (e.g. a compound) in singular, the plural is meant to be included. Thus, when referring to a specific moiety, e.g. "compound", this means "at least one" of that moiety, e.g. "at least one compound", unless specified otherwise.

As used herein, "halo" or "halogen" or even "halide" can refer to fluoro, chloro, bromo, and iodo.

As used herein, "alkyl" can refer to a straight-chain, branched, or cyclic saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), and the like. In various embodiments, an alkyl group can have 1 to 30 carbon atoms, for example, 1-20 carbon atoms (i.e., $C_1$-$C_{20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as defined herein. In some embodiments, substituted, saturated hydrocarbons, C1-C6 mono- and di- and pre-halogen substituted saturated hydrocarbons and amino-substituted hydrocarbons are preferred, with perfluoromethyl, perchloromethyl, perfluoro-tert-butyl, and perchloro-tert-butyl being the most preferred. The term "substituted alkyl" means any unbranched or branched, substituted saturated hydrocarbon, with unbranched C1-C6 alkyl secondary amines, substituted C1-C6 secondary alkyl amines, and unbranched C1-C6 alkyl tertiary amines being within the definition of "substituted alkyl," but not preferred. In some embodiments, the term "alkyl" means any unbranched or branched, substituted saturated hydrocarbon. In some embodiments, cyclic compounds, both cyclic hydrocarbons and cyclic compounds having heteroatoms, are within the meaning of "alkyl."

As used herein, "haloalkyl" can refer to an alkyl group having one or more halogen substituents. At various embodiments, a haloalkyl group can have 1 to 20 carbon atoms, for example, 1 to 10 carbon atoms (i.e., $C_1$-$C_{10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., perfluoroalkyl groups such as $CF_3$ and $C_2F_5$), are included within the definition of "haloalkyl."

As used herein, "alkoxy" can refer to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be substituted with 1-5 $R^1$ groups and $R^1$ is as defined herein.

As used herein, "carbocyclyl" can refer to a non-aromatic saturated or unsaturated monocyclic hydrocarbon ring, typically having from 3 to 6 carbon atoms. Preferably it is a saturated hydrocarbon ring (i.e. a cycloalkyl group) having from 3 to 6 carbon atoms. Examples include cyclopropyl, cyclobutyl, cyclopentyl and cyclohexyl. It is preferably cyclopentyl or cyclohexyl. A cycloalkyl group may be unsubstituted or substituted at any position. Typically, it carries 0, 1, 2 or 3 substituents.

As used herein, "heterocyclyl" or "heterocyclic" is a non-aromatic saturated or unsaturated carbocyclic ring typically having from 5 to 10 carbon atoms, in which one or more, for example 1, 2 or 3, of the carbon atoms is replaced by a heteroatom selected from N, O and S. A heterocyclic group may be unsubstituted or substituted at any position. Typically, it carries 0, 1 or 2 substituents.

As used herein, "alkenyl" means any unbranched or branched, substituted or unsubstituted, unsaturated hydrocarbon, with C1-C6 unbranched, mono-unsaturated and di-unsaturated, unsubstituted hydrocarbons being preferred, and mono-unsaturated, di-halogen substituted hydrocarbons being most preferred. In some embodiments, the term "alkenyl" means any unbranched or branched, substituted unsaturated hydrocarbon, substituted with one or more functional groups, with unbranched C2-C6 alkenyl secondary amines, substituted C2-C6 secondary alkenyl amines, and unbranched C2-C6 alkenyl tertiary amines being within the definition of "substituted alkyl." In some embodiments, the term "substituted alkenyl" means any unbranched or branched, substituted unsaturated hydrocarbon. In some embodiments, cyclic compounds, both unsaturated cyclic hydrocarbons and cyclic compounds having heteroatoms, are within the meaning of "alkenyl."

As used herein, the term "aryl" encompasses the terms "substituted aryl," "heteroaryl," and "substituted heteroaryl" which refer to aromatic hydrocarbon rings, preferably having five or six atoms comprising the ring. In some embodiments, the terms "heteroaryl" and "substituted heteroaryl" refer to aromatic hydrocarbon rings in which at least one heteroatom, for example, oxygen, sulfur, or nitrogen atom, is in the ring along with at least one carbon atom. "Aryl," most generally, and "substituted aryl," "heteroaryl," and "substituted heteroaryl" more particularly, refer to aromatic hydrocarbon rings, preferably having five or six atoms, and most preferably having six atoms comprising the ring. In some embodiments, the term "substituted aryl" includes mono and poly-substituted aryls, substituted with, for example, alkyl, aryl, alkoxy, azide, amine, and amino groups. "Heteroaryl" and "substituted heteroaryl," if used separately, specifically refer to aromatic hydrocarbon rings in which at least one heteroatom, for example, oxygen, sulfur, or nitrogen atom, is in the ring along with at least one carbon atom.

As used herein, "heteroatom" or "heteroatomic" can refer to an atom of any element other than carbon or hydrogen and includes, for example, nitrogen, oxygen, silicon, sulfur, phosphorus, and selenium.

As used herein, "heteroaryl" can refer to an aromatic monocyclic ring system containing at least one ring heteroatom selected from oxygen (O), nitrogen (N), sulfur (S), silicon (Si), and selenium (Se), or a polycyclic ring system wherein at least one of the rings present in the ring system is aromatic and contains at least one ring heteroatom. A heteroaryl group, as a whole, can have, for example, from 5 to 16 ring atoms and contain 1-5 ring heteroatoms (i.e., 5-16 membered heteroaryl group). In some embodiments, heteroaryl groups can be substituted with one or more terminal $R^1$ groups, where $R^1$ is as defined herein. Both substituted and unsubstituted heteroaryl groups described herein can comprise between 1-30, or 1-20 carbon atoms, including the $R^1$ substituents.

As used herein, "aryl" can refer to a broad variety of unsaturated cyclic groups which can provide conjugation and delocalization and can be fused and can be optionally substituted, as known in the art. Aryl groups with $C_6$ to $C_{40}$ or $C_6$ to $C_{30}$ in carbon number can be used, for example.

As used herein, "halo" or "halogen" can refer to F, Cl, Br, or I. It is preferably chlorine, fluorine or bromine. It is more preferably chlorine or fluorine.

One embodiment provides a compound represented by the Formula:

A-L-IS wherein A is a hydrophobic molecular delivery moiety, L is a linking moiety and IS is an iminosugar moiety or an analogue thereof. It is understood that the various moieties described individually and the moieties described within the Formulas recited below can each be included in the structure above in various combinations. Additionally, the A, L, and IS moieties can be analogues of those disclosed herein which are known in the art. For example, iminosugars and many iminosugar analogues are known in the art, for example in references cited herein, and are contemplated embodiments of the present invention.

One embodiment provides for a compound represented by formula XX' or a compound represented by formula YY'

XX'

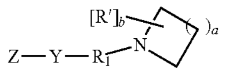

YY'

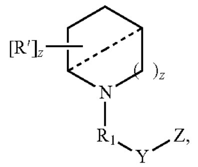

wherein:

$R_1$ is a linking moiety, preferably $(CH_2)_p$, optionally with one or more heteroatomic substitution or $(CH_2CH_2XCH_2CH_2)_q$;

p is an integer 2-20;

Y is a bond, $CH_2$, S, $N(R_3)$, or O;

Z is a hydrophobic molecular delivery moiety described herein, preferably a tocopherol, tocotrienol, cholesterol, ezetimibe, or an analogue thereof;

a represents an integer from 1 to 7, provided that the ring may also contain at least one unsaturated C—C bond where n>1. b represents an integer from 1 to (a+2). y represents either 1 or 2, and z represents an integer from 1 to (y+7). R' represents OH; OR"; =O; $NH_2$; $N_3$; SH; $SO_xR$"; halo; CN; $NO_2$; NR"$R^3$; (NR")NR"$R^3$; NH(NR")NR"$R^3$; $CO_2R^3$; CONR"$R^3$; $NR^3COR$"; $NR^3SO_2R$"; $P(O)(OR")_2$; C1-15 alkyl or alkenyl optionally substituted with one or more OH, OR", =O, $NH_2$, $N_3$, SH, $SO_xR$", halo, CN, $NO_2$, NR"$R^3$, (NR")NR"$R^3$, NH(NR")NR"$R^3$, $CO_2R^3$, CONR"$R^3$, $NR^3COR$", $NR^3SO_2R$", $P(O)(OR")_2$, aryl or carbocyclyl groups; carbocyclyl or aryl, either of which is optionally substituted with one or more OH, OR", =O, $NH_2$, $N_3$, SH, $SO_xR^3$, halo, CN, $NO_2$, NR"$R^3$, (NR")NR"$R^3$, NH(NR")NR"$R^3$, $CO_2R^3$, CONR"$R^3$, $NR^3COR$", $NR^3SO_2R$", $P(O)(OR")_2$, C1-9 alkyl optionally substituted with one or more OH, OR", =O, $NH_2$, $N_3$, halo, CN, $NO_2$, NR"$R^3$, $CO_2R^3$, CONR"$R^3$, aryl or carbocyclyl groups; O-glycosyl; C-glycosyl; O-sulfate; O-phosphate or a group which together with the endocyclic carbon forms a spiro ring, with the provisos that (a) two OH groups may not be attached to the same endocyclic carbon atom; (b) where there is only one R' substituent it contains an oxygen atom directly bonded to an endocyclic carbon atom; and (c) where b or z>1 any two R' substituents may together form an optionally heterocyclic ring (for example, a carbocycle, cyclic ether or acetal). R" represents H; C1-6 alkyl, optionally substituted with one or more OH; aryl or C1-3 alkyl optionally substituted with aryl; $SiR^3_3$. $R^3$ represents H; C1-6 alkyl, optionally substituted with one or more OH. R" and $R^3$ may optionally form a 4 to 8 membered ring, containing one or more O, $SO_X$-or $NR^3$ groups. X represents an integer from 0 to 2 (inclusive). The dotted line in structure YY represents an optional bridge containing 2 or 3 carbon atoms between any two different ring carbon atoms, any or all of which bridge or bridgehead carbon atoms being optionally substituted with R'. Without being bound by theory, Applicants believe these various groups have the ability to tune the hydrogen bonding ability of the ring, as well as the acidity of the endocyclic nitrogen. One embodiment provides for a compound represented by formula YY' or a pharmaceutically acceptable salt, solvate, prodrug or derivatives thereof. One embodiment provides for a compound represented by formula XX' or a pharmaceutically acceptable salt, solvate, prodrug or derivatives thereof.

Another embodiment provides for a compound of the formula (I'):

(I')

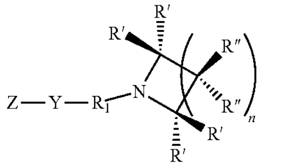

wherein:

R' is, independently in each instance, H, $(CH_2)_mCH_3$, $(CH_2)_mCH_2OH$, $(CH_2)_mCH_2NH_2$, $(CH_2)_mCH_2NHAc$, $(CH_2)_mCH_2F$, $(CH_2)_mCH_2Cl$;

R" is, independently in each instance, H, OH, $NH_2$, $(CH_2)_m CH_3$, NHAc, F, Cl;

$R_1$ is $(CH_2)_p$, optionally with one or more heteroatomic substitution or $(CH_2CH_2XCH_2CH_2)_q$;

Y is a bond, $CH_2$, S, $N(R_3)$, or O;

Z is a tocopherol, tocotrienol, cholesterol, ezetimibe, or an analogue thereof;

m is 0 or an integer 1-5;

n is 1, 2, 3, 4, 5, 6 or 7.

p is an integer 2-20 q is an integer 1-20

X is, in each instance, O, S, or $N(R_3)$, wherein $R_3$ is H or a $C_1$-$C_{20}$ alkyl;

or a pharmaceutically acceptable salt, solvate, prodrug or derivatives thereof.

One embodiment provides, for example A compound having formula I:

(I)

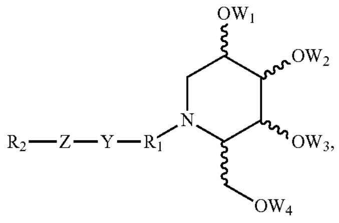

wherein:

$R_1$ is $C_2$-$C_6$ alkyl or oxaalkyl group;

Y is O or $CH_2$;

Z is selected from $(CH_2)_3$—O—$CH_2$, $(CH_2)_5$,

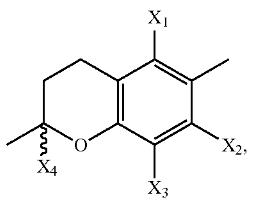

and

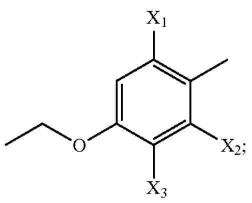

$R_2$ is (a) straight or branched $C_{10}$-$C_{16}$ alkyl or alkylene groups and H, when Z is

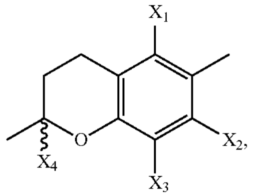

and (b) straight or branched $C_{10}$-$C_{20}$ alkyl or alkylene groups, when Z is $(CH_2)_3$—O—$CH_2$; $(CH_2)_5$ or

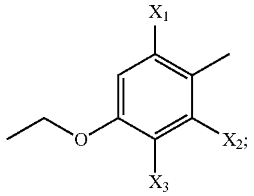

$W_{1-4}$ are each independently selected from H or an alcohol protecting group; and $X_{1-4}$ are each independently selected from H or $C_{1-2}$ alkyl.

In one embodiment, "$OW_{1-4}$" are represented by the moieties of R' in Formulas XX, YY, XX' or YY'.

In another embodiment, the compound of Formula I is represented by a compound of Formula II (II)

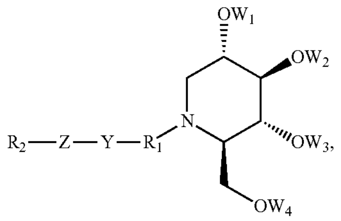

wherein $R_1$, $R_2$, Z, Y and $W_{1-4}$ are previously defined.

In another embodiment, the $R_1$ is $C_3$-$C_5$ alkyl optionally substituted by one or more heteroatoms. In one embodiment, "$OW_{1-4}$" are represented by the moieties of R' in Formulas XX, YY, XX' or YY'.

In another embodiment, Formula I is steoisomerically pure. For example, the substitution on the iminosugar ring is set; included are for example, the moieties, or derivatives of, deoxygalactonojirimycin (DGJ), derivatives of deoxynojirimycin (DNJ), deoxyfuconojirimycin (DFJ), deoxymannojirimycin (DMJ), In considering the covalent attachment of tocopherol to an iminosugar, it becomes immediately apparent that the molecule would behave differently in a number of physical and biological ways from previously described alkyl and alkoxy iminosugars, as follows:—

1. Tocopherol is taken up efficiently in the gut, commensurate with its status as an essential vitamin. A tocopheryl iminosugar would be expected to be taken up in the same way as tocopherol, i.e. different from conventional iminosugars which are taken up (albeit efficiently) by passive diffusion.
2. Tocopherol, as an iminosugar appendage, has the potential to reduce osmotic diarrhea associated with other iminosugar drugs (viz Zavesca), by forming stable micelles with bile salts (as does cholesterol), limiting the gut-availability of the active iminosugar headgroup moiety from interacting with and inhibiting sucrase-isomaltase. Moreover, the positive charge on the iminosugar nitrogen would enhance the stability of these bile salt micelles, reducing the bioavailability of the active moiety in the gut, by interacting with the negatively charged carboxylate of deoxycholate. This feature would allow higher doses to be administered than for conventional lipophillic (as distinct from 'lipidic') iminosugars.
3. Tocopherol is remarkably non-toxic having been used in high doses for years at a time in clinical studies of atherosclerosis and Parkinson's disease with striking lack of toxicity (or efficacy). Metabolic liberation of tocopherol from a tocopheryl iminosugar would likely avoid the toxicity of comparable alternative/xenobiotic appendages.
4. Tocopherol is clinically effective in the treatment of steatosis (triglyceride accumulation) in the context of non-alcoholic fatty liver disease (more effective than Pioglitazone) (**NEJM ref). Steatosis is also a feature of hepatitis-C virus genotype-III. Generally (independent of genotype) hepatitis-C virus manipulates cellular lipid metabolism to its own advantage. Possibly, the clinical effect of tocopherol would be embodied also in tocopheryl iminosugars, to antiviral effect, creating a molecule with dual mechanism of action.
5. Tocopherol is packaged by gut epithelial cells into chylomicrons which permeate the lymphatic system first, before entering the blood circulation (in contrast to conventional drugs which enter the bloodstream first and are prone to first-pass elimination in the liver before they can exert therapeutic effect). Tocopheryl iminosugars would be expected to take the same route of distribution in the body. Although first pass metabolic destruction by the liver would not be a major problem for iminosugars in general, avoidance of first pass elimination in the liver also involves excretion into the bile which would be avoided for this new class of iminosugar.
6. Packaging of tocopheryl-iminosugar into the lipid phase of chylomicrons would eliminate the rapid excretion from the circulation via the kidney which characterizes more hydrophillic drugs which occupy or pass through the aqueous phase of the circulation before they can act on target cells. Moreover this disposition of the tocopheryl iminosugar facilitates delivery to cells, in the same way that dietary cholesterol and dietary tocopherol are delivered.
7. Inside the liver cell, in the case of hepatitis-C virus, the tocopheryl iminosugar would be expected to compete with viral cholesterol for endosomal escape of the virus, which is dependent on the cholesterol receptor protein NPCL1, much as Ezitimibe (another competitor at NPCL1 for cholesterol binding) does.
8. The R,R,R-alpha-tocopherol form (as distinct from other dietary tocols which are eliminated in the bile) is retained in the liver and repackaged into lipoproteins, providing a 'second life' for the drug in circulation, tending to elevate blood concentrations and longevity of circulation of the drug.
9. Within liver cells, tocopheryl iminosugars would be expected to be transported in the aqueous phase by tocopherol transfer protein, facilitating distribution of tocopheryl iminosugar to all membranes of the cell as for tocopherol per se 10. Tocopherol is an integral component of membrane bilayers, therefore a tocopheryl-iminosugar would tend to inhabit the membrane phase of cells—rather than being 'lipophillic' the molecule would be 'lipidic', having a much stronger tendency to insert and remain stably incorporated into membranes
11. Tocopherol can 'flip-flop' across membrane bilayers (ref**), in a manner analogous to that of dolichol phosphate and its glycan derivatives, allowing better penetration of target membrane compartments (such as the ER) for tocopheryl iminosugars
12. Tocopherol is concentrated naturally into the ER and lipid droplet of cells (*ref) facilitating delivery of tocopheryl iminosugars to cellular compartments and organelles of relevance to virus infection (particularly hepatitis-C)
13. The tocopherol moiety, if it becomes metabolized to tocopherol, an antioxidant, would be expected to counteract the oxidative free radical induced damage inflicted by hepatitis-C virus infection in infected cells (*ref), allowing such cells to function more effectively for the better health of the patient The structure and synthesis of the 'tocopheryl-DNJ' molecule, archetype of the lipidic-iminosugars of this invention, is shown in FIG. 1. An exemplary synthesis is described in the Working Examples. As labeled in the in FIG. 1**, the structure of this class of iminosugars may be divided into three distinct regions: an iminosugar headgroup (DNJ in the archetype), a linker, and a chemophore (here, D-α-tocopherol) that imparts the lipid nature to the molecule.

Iminosugar Moiety

Iminosugars are generally known in the art. For example, see, Block, T. M., et al. Secretion of Human Hepatitis B Virus is Inhibited by the Imino Sugar N-Butyldeoxynojirimycin. *PNAS* 91, 2235-2239 (1994); Fischer, P. B., et al. The alpha-glucosidase inhibitor N-butyldeoxynojirimycin inhibits human immunodeficiency virus entry at the level of post-CD4 binding. *J. Virol.* 69, 5791-5797 (1995); Jordan, R., et al. Inhibition of Host ER Glucosidase Activity Prevents Golgi Processing of Virion-Associated Bovine Viral Diarrhea Virus E2 Glycoproteins and Reduces Infectivity of Secreted Virions. *Virology* 295, 10-19 (2002); Wu, S.-F., et al. Antiviral Effects of an Iminosugar Derivative on Flavivirus Infections. *J. Virol.* 76, 3596-3604 (2002); Tanaka, Y., Kato, J., Kohara, M. & Galinski, M. S. Antiviral effects of glycosylation and glucose trimming inhibitors on human parainfluenza virus type 3. *Antiviral Research* 72, 1-9 (2006); Chapel, C., et al. Reduction of the infectivity of hepatitis C virus pseudoparticles by incorporation of misfolded glycoproteins induced by glucosidase inhibitors. *J Gen Virol* 88, 1133-1143 (2007); Aizaki, H., et al. Critical Role of Virion-Associated Cholesterol and Sphingolipid in Hepatitis C Virus Infection. *J Virol.* 82, 5715-5724 (2008); Ono, A. & Freed, E. O. Plasma membrane rafts play a critical role in HIV-1 assembly and release. *Proc Natl Acad Sci USA.* 98, 13925-13930 (2001); Popik, W. & Alce, T. M. CD4 Receptor Localized to Non-raft Membrane Microdomains Supports HIV-1 Entry: Identification of a novel raft localization marker in CD4. *J Biol Chem.* 279, 704-712 (2004); Campbell, S. M., Crowe, S. M. & Mak, J. Virion-associated cholesterol is critical for the maintenance of HIV-1 structure and infectivity. *AIDS* 16, 2253-2261 (2002); Guyader, M., Kiyokawa, E., Abrami, L., Turelli, P. & Trono, D. Role for Human Immunodeficiency Virus Type 1 Membrane Cholesterol in Viral Internalization. *J Virol.* 76, 10356-10364 (2002); Bavari, S., et al. Lipid Raft Microdomains: A Gateway for Compartmentalized Trafficking of Ebola and Marburg Viruses. *J Exp Med.* 195, 593-602 (2002); Vincent, S., Gerlier, D. & Manie, S. N. Measles Virus Assembly within Membrane Rafts. *J Virol.* 74, 9911-9915 (2000); Scheiffele, P., Rietveld, A., Wilk, T. & Simons, K. Influenza Viruses Select Ordered Lipid Domains during Budding from the Plasma Membrane. *J Biol Chem.* 274, 2038-2044 (1999); Leser, G. P. & Lamb, R. A. Influenza virus assembly and budding in raft-derived microdomains: A quantitative analysis of the surface distribution of HA, NA and M2 proteins. *Virology* 342, 215-227 (2005); H., Lee, K.-J., Sung, V. M. H., Ishiko, H. & Lai, M. M. C. Characterization of the hepatitis C virus RNA replication complex associated with lipid rafts. *Virology* 324, 450-461 (2004); Pollock, S., Dwek, R. A., Burton, D. R. & Zitzmann, N. N-Butyldeoxynojirimycin is a broadly effective anti-HIV therapy significantly enhanced by targeted liposome delivery. *AIDS* 22, 1961-1969 (2008); Leu, G.-Z., Lin, T.-Y. & Hsu, J. T. A. Anti-HCV activities of selective polyunsaturated fatty acids. *Biochem Biophys Res Commun.* 318, 275-280 (2004). Each of which is hereby incorporated by reference in its entirety as enabling disclosure for the entire application.

In an embodiment, the iminosugar or iminosugar analogue is represented by the formula XX or YY:

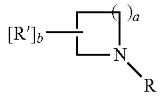

XX

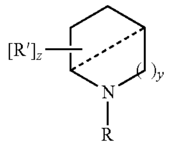

YY wherein R is the a covalent bond to the linking moiety. Alkylation performed by analogous reductive amination to the archetypical compound a represents an integer from 1 to 7, provided that the ring may also contain at least on unsaturated C—C bond where n>1. b represents an integer from 1 to (a+2). y represents either 1 or 2, and z represents an integer from 1 to (y+7). R' represents OH; OR"; =O; $NH_2$; $N_3$; SH; $SO_xR$"; halo; CN; $NO_2$; NR"$R^3$; (NR")NR"$R^3$; NH(NR")NR"$R^3$; $CO_2R^3$; CONR"$R^3$; $NR^3$COR"; $NR^3SO_2R$"; P(O)(OR")$_2$; C1-15 alkyl or alkenyl optionally substituted with one or more OH, OR", =O, $NH_2$, $N_3$, SH, $SO_xR$", halo, CN, $NO_2$, NR"$R^3$, (NR")NR"$R^3$, NH(NR")NR"$R^3$, $CO_2R^3$, CONR"$R^3$, $NR^3$COR", $NR^3SO_2R$", P(O)(OR")$_2$, aryl or carbocyclyl groups; carbocyclyl or aryl, either of which is optionally substituted with one or more OH, OR", =O, $NH_2$, $N_3$, SH, $SO_xR^3$, halo, CN, $NO_2$, NR"$R^3$, (NR")NR"$R^3$, NH(NR")NR"$R^3$, $CO_2R^3$, CONR"$R^3$, $NR^3$COR", $NR^3SO_2R$", P(O)(OR')$_2$, C1-9 alkyl optionally substituted with one or more OH, OR", =O, $NH_2$, $N_3$, halo, CN, $NO_2$, NR"$R^3$, $CO_2R^3$, CONR"$R^3$, aryl or carbocyclyl groups; O-glycosyl; C-glycosyl; O-sulfate; O-phosphate or a group which together with the endocyclic carbon forms a spiro ring, with the provisos that (a) two OH groups may not be attached to the same endocyclic carbon atom; (b) where there is only one R' substituent it contains an oxygen atom directly bonded to an endocyclic carbon atom; and (c) where b or z>1 any two R' substituents may together form an optionally heterocyclic ring (for example, a carbocycle, cyclic ether or acetal). R" represents H; C1-6 alkyl, optionally substituted with one or more OH; aryl or C1-3 alkyl optionally substituted with aryl; $SiR^3_3$. $R^3$ represents H; C1-6 alkyl, optionally substituted with one or more OH. R" and $R^3$ may optionally form a 4 to 8 membered ring, containing one or more O, $SO_X$ or $NR^3$ groups. X represents an integer from 0 to 2 (inclusive). The dotted line in structure YY represents an optional bridge containing 2 or 3 carbon atoms between any two different ring carbon atoms, any or all of which bridge or bridgehead carbon atoms being optionally substituted with R'. Without being bound by theory, Applicants believe these various groups have the ability to tune the hydrogen bonding ability of the ring, as well as the acidity of the endocyclic nitrogen. The iminosugar moieties embodied herein include iminosugars or iminosugar analogues known in the art, as well as novel iminosugar or iminosugar analogues embodied herein. In one embodiment, the iminosugar moiety is attached to the linking moiety through a covalent bond between an atom of the linking moiety and a nitrogen atom of the core iminosugar ring.

In one embodiment, the iminosugar moiety is represented by the following structure:

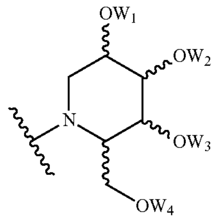

wherein $W_{1-4}$ are each independently a hydrogen, $C_{1-20}$ alkyl, alcohol protecting group or a cation. In one embodiment, $W_{1-4}$ are each independently a hydrogen or $C_{1-10}$ alkyl for example, the moieties, or derivatives of, deoxygalactonojirimycin (DGJ), derivatives of deoxynojirimycin (DNJ), deoxyfuconojirimycin (DFJ), deoxymannojirimycin (DMJ), and the like. In one embodiment, "$OW_{1-4}$" are represented by the moieties of R' in Formulas XX, YY, XX' or YY'.

In one embodiment, the iminosugar moiety is represented by the following structure:

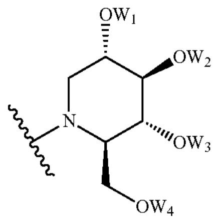

wherein $W_{1-4}$ are each independently a hydrogen, $C_{1-20}$ alkyl, alcohol protecting group or a cation. In one embodiment, $W_{1-4}$ are each independently a hydrogen or $C_{1-2}$ alkyl. In one embodiment, "$OW_{1-4}$" are represented by the moieties of R' in Formulas XX, YY, XX' or YY'.

In addition to the iminosugars shown above, other known iminosugars, obtainable both from natural sources and synthetic means, may be used in the place of the head group including stereoisomers and heterosubstitutions of deoxynojirimycin and homonojirimycin (2), pyrrolidines (3), azetidines (4), azepanes (5), and 8-membered iminocyclitols (6). In all cases, the linker moiety or hydrophobic chemophoric appendage is connected via the third valence of the endocyclic nitrogen atom. The examples shown herein are not meant to be exhaustive, but representative. Other iminocyclitols, which may be alkylated in an analogous way, as would be clear to one skilled in the art, are also understood to be embodied within the invention.

The iminosugar moiety is not limited to the six-membered iminosugar rings embodied in the preceding figures. In other embodiments, the iminosugar moiety is an iminosugar or iminosugar analogue with a core ring comprising 3 to 7 carbons. In another embodiment, the iminosugar or iminosugar analogue is represented by any one of the following compounds:

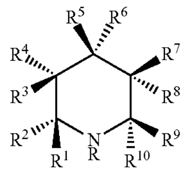

2

$R^1$ = H, F, $CH_3$, $CH_2OH$, $CH_2NH_2$, $CH_2NHAc$, $CH_2F$, $CH_2Cl$
$R^2$ = H, F, $CH_3$, $CH_2OH$, $CH_2NH_2$, $CH_2NHAc$, $CH_2F$, $CH_2Cl$
$R^3$ = H, OH, $NH_2$, NHAc, F, Cl, $CH_3$
$R^4$ = H, OH, $NH_2$, NHAc, F, Cl, $CH_3$
$R^5$ = H, OH, $NH_2$, NHAc, F, Cl, $CH_3$
$R^6$ = H, OH, $NH_2$, NHAc, F, Cl, $CH_3$
$R^7$ = H, OH, $NH_2$, NHAc, F, Cl, $CH_3$
$R^8$ = H, OH, $NH_2$, NHAc, F, Cl, $CH_3$
$R^9$ = H, F, $CH_3$, $CH_2OH$, $CH_2NH_2$, $CH_2NHAc$, $CH_2F$, $CH_2Cl$
$R^{10}$ = H, F, $CH_3$, $CH_2OH$, $CH_2NH_2$, $CH_2NHAc$, $CH_2F$, $CH_2Cl$

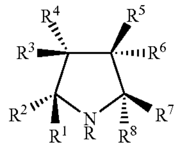

3

$R^1$ = H, F, $CH_3$, $CH_2OH$, $CH_2NH_2$, $CH_2NHAc$, $CH_2F$, $CH_2Cl$
$R^2$ = H, F, $CH_3$, $CH_2OH$, $CH_2NH_2$, $CH_2NHAc$, $CH_2F$, $CH_2Cl$
$R^3$ = H, OH, $NH_2$, NHAc, F, Cl, $CH_3$
$R^4$ = H, OH, $NH_2$, NHAc, F, Cl, $CH_3$
$R^5$ = H, OH, $NH_2$, NHAc, F, Cl, $CH_3$
$R^6$ = H, OH, $NH_2$, NHAc, F, Cl, $CH_3$
$R^7$ = H, F, $CH_3$, $CH_2OH$, $CH_2NH_2$, $CH_2NHAc$, $CH_2F$, $CH_2Cl$
$R^8$ = H, F, $CH_3$, $CH_2OH$, $CH_2NH_2$, $CH_2NHAc$, $CH_2F$, $CH_2Cl$

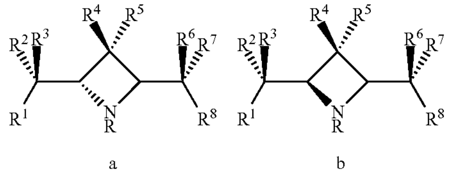

4 a b $R^1$ = H, $CH_3$, $CH_2OH$, $CH_2NH_2$, $CH_2NHAc$, $CH_2F$, $CH_2Cl$
$R^2$ = H, OH, $NH_2$, NHAc, F, Cl, $CH_3$
$R^3$ = H, OH, $NH_2$, NHAc, F, Cl, $CH_3$
$R^4$ = H, OH, $NH_2$, NHAc, F, Cl, $CH_3$
$R^5$ = H, OH, $NH_2$, NHAc, F, Cl, $CH_3$
$R^6$ = H, OH, $NH_2$, NHAc, F, Cl, $CH_3$
$R^7$ = H, OH, $NH_2$, NHAc, F, Cl, $CH_3$
$R^8$ = H, $CH_3$, $CH_2OH$, $CH_2NH_2$, $CH_2NHAc$, $CH_2F$, $CH_2Cl$

-continued

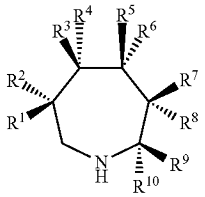

5

$R^1$ = H, OH, $NH_2$, NHAc, F, Cl, $CH_3$
$R^2$ = H, OH, $NH_2$ NHAc, F, Cl, $CH_3$
$R^3$ = H, OH, $NH_2$, NHAc, F, Cl, $CH_3$
$R^4$ = H, OH, $NH_2$, NHAc, F, Cl, $CH_3$
$R^5$ = H, OH, $NH_2$, NHAc, F, Cl, $CH_3$
$R^6$ = H, OH, $NH_2$, NHAc, F, Cl, $CH_3$
$R^7$ = H, OH, $NH_2$, NHAc, F, Cl, $CH_3$
$R^8$ = H, OH, $NH_2$, NHAc, F, Cl, $CH_3$
$R^9$ = H, F, $CH_3$, $CH_2OH$, $CH_2NH_2$, $CH_2NHAc$, $CH_2F$, $CH_2Cl$
$R^{10}$ = H, F, $CH_3$, $CH_2OH$, $CH_2NH_2$, $CH_2NHAc$, $CH_2F$, $CH_2Cl$

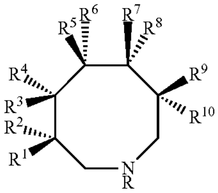

6

$R^1$ = H, OH, $NH_2$, NHAc, F, Cl, $CH_3$
$R^2$ = H, OH, $NH_2$ NHAc, F, Cl, $CH_3$
$R^3$ = H, OH, $NH_2$, NHAc, F, Cl, $CH_3$
$R^4$ = H, OH, $NH_2$, NHAc, F, Cl, $CH_3$
$R^5$ = H, OH, $NH_2$, NHAc, F, Cl, $CH_3$
$R^6$ = H, OH, $NH_2$, NHAc, F, Cl, $CH_3$
$R^7$ = H, OH, $NH_2$, NHAc, F, Cl, $CH_3$
$R^8$ = H, OH, $NH_2$, NHAc, F, Cl, $CH_3$
$R^9$ = H, F, $CH_3$, $CH_2OH$, $CH_2NH_2$, $CH_2NHAc$, $CH_2F$, $CH_2Cl$
$R^{10}$ = H, F, $CH_3$, $CH_2OH$, $CH_2NH_2$, $CH_2NHAc$, $CH_2F$, $CH_2Cl$ wherein R represents a covalent bond between the nitrogen and the linking moiety.

It is appreciated that the $R_1$ to $R_{10}$ groups are not limited to those shown above. In another embodiment, each of $R_1$ to $R_{10}$ is independently selected from the moieties of R', as defined for Formula XX, XX', YY' or YY.

In addition to the parent iminosugar and iminosugar analogue moieties embodied herein, pharmaceutically acceptable salts, solvates or derivatives thereof, which are present in the pharmaceutical compound are also embodied herein.

Linker Moiety

The nature of the linker is based on a series of features that were carefully considered. First of all, the connection points to the iminosugar and tocopherol moieties. As mentioned above, this means alkylation of the endocyclic nitrogen for incorporation of the iminosugar. In conjugating the tocopherol, the hydroxyl group of the chromanol ring was selected. Because the concept is to design lipid-inspired iminosugars, it is desirable for the final molecule to have a hydrophobic side and separate hydrophilic side. As the polyhydroxylated structure of iminosugars makes them hydrophilic, this design places them close to the natural hydrophilic head of tocopherol. Furthermore, the hydroxyl group of tocopherol is involved in its antioxidant activity. While this activity is often beneficial in vivo, it also imparts concerns with regard to long-term stability. By involving the functional group in an ether bond, the propensity for redox chemistry is diminished, making the compound more stable. Finally, the chemical nature of the oxygen made it a convenient place for modification.

In the Working Example, a 5-carbon aliphatic spacer has been incorporated between the oxygen atom of the tocopherol headgroup and the endocyclic nitrogen atom of the iminosugar. The spacer is designed to allow sterically unhindered engagement of the molecular target sites, be they, for example, the active sites of glucosidase-I and glucosidase-II, or other cellular enzymes, or non-enzymatic targets such as lysine or arginine residues of various ion channels. However, the invention also includes molecules with both longer and shorter linkers as shown, for example, in FIG. 2, structures 7. Also, a strictly carbon chain, being hydrophobic in nature, could, if too long, break up the hydrophilic region of the molecule. To maintain the concept of a single hydrophilic and hydrophobic region, replacement of one or more methylene groups with heteroatoms is also possible in this structure, shown, for example, in FIG. 2, structures 8-11. By strategically placing these heteroatoms, one also gains the ability to tune both the iminosugar pKa (acidity) as well as the possibility of inducing secondary structure via intramolecular hydrogen bonds, FIG. 3. This modification may also lead to enhanced availability of the active iminosugar moiety to target sites (by virtue of increased hydrophillicity of the linker) or to lesser availability of the compound due to hindered crossing of cellular membranes, as per multi-oxy-alkyl chain DNJ molecules.

The linker moiety covalently bonds to the iminosugar or iminosugar analogue moiety and the hydrophobic chemophoric appendage. In one embodiment, the linker is a covalent bond. In another embodiment, the linker is a $C_1$ though $C_5$ alkyl, oxaalkyl or alkoxy moiety or a $C_2$ though $C_5$ alkyl, oxaalkyl or alkoxy moiety, or a $C_3$ though $C_5$ alkyl, oxaalkyl or alkoxy moiety, or a $C_4$ though $C_5$ alkyl, oxaalkyl or alkoxy moiety, or a $C_2$ though $C_6$ alkyl, oxaalkyl or alkoxy moiety, or a $C_3$ though $C_6$ alkyl or alkoxy moiety, or a $C_4$ though $C_6$ alkyl, oxaalkyl or alkoxy moiety, or a $C_5$ though $C_6$ alkyl or alkoxy moiety, or a $C_2$ though $C_{10}$ alkyl, oxaalkyl or alkoxy moiety, or a $C_3$ though $C_{20}$ alkyl or alkoxy moiety. In each embodiment, the alkyl, oxaalkyl or alkoxy moiety is optionally substituted by one or more additional heteroatom, such as oxygen, sulfur and/or nitrogen, or other moiety capable of hydrogen bonding in a manner analogous to FIG. 4.

In other embodiments the linker moiety is represented by "$R_1$" in Formulas XX, XX', YY' and YY. In other embodiments the linker moiety is represented by R' in Formulas I and II. In other embodiments, the linker moieties comprise those shown in the Figures.

Hydrophobic Chemophoric Appendage

The hydrophobic chemophoric appendage comprises at least one lipid-mimicking tail. In one embodiment, the hydrophobic chemophoric appendage is tocopherol. In addition to the use of tocopherol as an exemplary chemophoric appendage to the nitrogen atom of the iminosugar, there are other moieties that are embodied herein. Namely the anti-cholesterol drug Ezitimibe, which acts to inhibit the uptake of cholesterol in the gut.

Cholesterol iminosugars have been developed as experimental tools (Aerts**). These molecules would have many of the properties of a tocopheryl-iminosugar. However, with cholesterol as a molecular drug delivery module/moiety, in place of tocopherol, there is a risk that cholesterol would be liberated by metabolic degradation to undesirable effects. Notably, it is known that many viruses depend upon cholesterol in cellular membranes for part or parts of their life cycle, and enveloped viruses typically contain high concentrations of cholesterol in their lipidic envelopes. See, e.g., Aizaki, H., et al. Critical Role of Virion-Associated Cholesterol and Sphingolipid in Hepatitis C Virus Infection. *J Virol.* 82, 5715-5724 (2008); Campbell, S. M., Crowe, S. M. & Mak, J. Virion-associated cholesterol is critical for the maintenance of HIV-1 structure and infectivity. *AIDS* 16, 2253-2261 (2002); Guyader, M., Kiyokawa, E., Abrami, L., Turelli, P. & Trono, D. Role for Human Immunodeficiency Virus Type 1 Membrane Cholesterol in Viral Internalization. *J Virol.* 76, 10356-10364 (2002). Cholesterol derivatives share the potential advantage of tocopheryl iminosugar derivatives in being taken up via NPCL1 cholesterol receptors in the gut, and being transported in the blood via lipoproteins, which may offset these disadvantages. Thus, in an embodiment, the hydrophobic chemophoric appendage comprises at least one cholesterol derivative.

However, distinct from cholesterol per se (which is a proviral substance), as a molecular delivery module and moiety of iminosugar drugs there are other sterols which are expected, according to the invention, to form favorable molecular modules or chemophores for the delivery of iminosugar drugs. Notably 25-hydroxycholesterol, which, unlike cholesterol, is antiviral. Yamamoto 2011 describes other variants of cholesterol that lack the proviral effect of cholesterol and which according to the invention would be useful as molecular delivery modules for antiviral iminosugar drugs, and are incorporated by reference as embodiments of the hydrophobic chemophoric appendage. In another embodiment, cholesterol derivatives are the following analogues with changes in the planar ring structure part of cholesterol: 4-cholestenone, cholesteryl acetate, cholesteryl methyl ether, 5-alpha-cholestane, ergosterol and 7-dehydrocholesterol. Likewise aliphatic chain derivatives such as sitosterol and ergosterol would be suitable moieties, and are embodiments of the present invention and of cholesterol derivatives. It is further understood that this is not a limiting list of aliphatic chain derivatives, and one of skill in the art would understand other aliphatic chain derivatives to be embodied by the present invention. Furthermore it can be seen from these statements that, paradoxically, cholesterol itself would form suitable moiety for iminosugar drugs, provided that it were attached to the iminosugar by a metabolically stable bond, such as an ether or an amide or a linker.

Likewise lipid moieties, such as diacylglyceryl iminosugars, analogous to diacylglyceryl-polyethylene glycol (NOF**), can be used as appendages for iminosugars, and thus as hydrophobic chemophoric appendages. A wide variety of acyl chain types (fatty acids) can be considered as moieties for these iminosugars, as can the number of chains (one or two) and, for single chain derivatives, the position of the chain, sn1 or sn2. Given that polyunsaturated fatty acids are intrinsically antiviral (eg. docosaheaenoic acid, 'DHA', which is an omega-3 polyunsaturated fatty acid 18), it can be anticipated that the most active such molecules would be those having DHA chains. Thus, in an embodiment the chemophoric appendage comprises a polyunsaturated fatty acid. In one embodiment, such compounds would be formulated with trace quantities (1% or less weight for weight) of R,R,R-alpha-tocopherol, or synthetic racemic tocopherols, as antioxidant, most favorably in gelatin capsules, such as for cod-liver oil. Likewise monounsaturated fatty acyl chains and saturated fatty acyl chains would also be useful, most favorably with lengths in the 18-22 region, in number of carbon atoms. Diacylglyceryl iminosugars, having the ability to form an uncharged headgroup via loss of a proton, would retain the 'flip-flop' ability of the prototypic tocopheryl-iminosugar tocopheryl-DNJ, which is advantageous, and are a present embodiment.

Further lipid moieties that are embodied herein as molecular delivery agents for iminosugars would be the acidic phospholipids phosphatidylserine (PS) and phosphatidylinositol (PI). In the case of PS, derivatives can be made taking advantage of the reactivity of the amino-group of the serine headgroup. In the case of phosphatidylinositol, methods have been described to make phosphatidyl inositol based iminosugars (e.g. Orsato A, 2011, Eur J Org Chem) which is incorporated by reference. These forms would not retain the ready 'flip-flop' character of the earlier series above, presumably because of the permanent negative charge on the phosphate moiety, but likely additionally would have the tendency to translocate to the ER of target cells upon cellular internalization, and likely would be transported across cellular membrane bilayers by 'flippases' that maintain the lipid asymmetry of the plasma membrane of living cells.

In some embodiments, Z is the hydrophobic chemophoric appendage and is

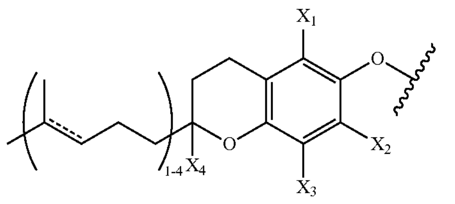

wherein X1-4 are each methyl and R1 is C5 alkyl and the dashed line represents an optional double bond or Z is

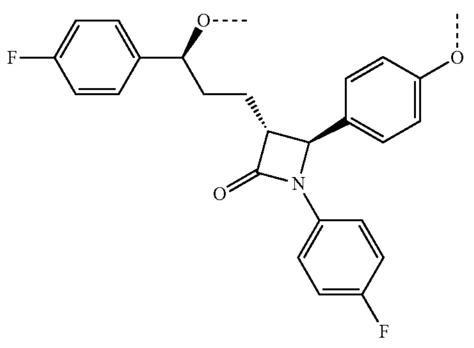

and at least one of the dashed lines represents a bond to the linker group or Z is a cholesterol derivative or Z is a diacylg lyceryl derivative or Z is Z"—$R_2$, wherein Z; is selected from $(CH_2)_3$—O—$CH_2$; $(CH_2)_5$;

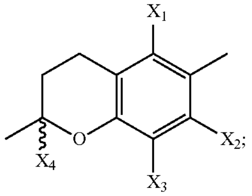

and

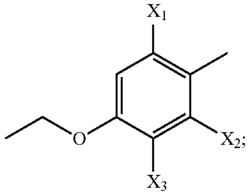

$R_2$ is a) a straight or branched $C_{10}$-$C_{16}$ alkyl or alkylene groups and H, when Z is

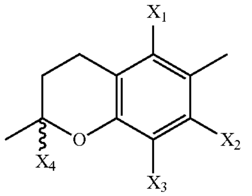

and b) a straight or branched $C_{10}$-$C_{20}$ alkyl or alkylene groups, when Z is $(CH_2)_3$—O—$CH_2$; $(CH_2)_5$ or

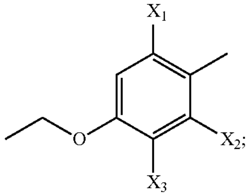

and $X_{1-4}$ are each independently selected from H or $C_{1-2}$ alkyl.

FIG. 5 shows, a number of embodied alternative variants for the tocopherol chemophore appendage. These include the unnatural stereoisomers of α-tocopherol, the various stereoisomers of β-, γ-, and δ-tocopherol (12-14), stereoisomers of α-, β-, γ-, and δ-tocotrienols (15-18), representative cholesterol analogues (21, 22) and Ezitimibe (23).

Synthetic Methods

Synthetic methods use for synthesizing the embodied compounds are known in the art and are also embodied in the Working Examples. The Working Examples are not intended to be limiting, and various analogous known reactions or analogous intermediates are also envisioned as embodied herein. For example, various analogous reagents or protecting groups, known to those of skill in the art, are also understood to be embodied herein. Important synthetic methods which can be used as appropriate herein to prepare compounds are generally described in *March's Advanced Organic Chemistry*, 6th Ed., 2007.

Formulations

The compounds of this invention can be utilized therapeutically. The amount of active ingredient for therapeutic administration can vary over a wide range and is dependent upon such factors as the species of mammal to be treated, its age, health, sex, weight, nature and the severity of the condition being treated.

Provided herein are pharmaceutical formulations for oral administration. Such oral pharmaceutical formulations may be prepared by any method known or hereafter developed in the art of pharmacology (see, e.g., Remington's Pharmaceutical Sciences, Sixteenth Edition, E. W. Martin, Mack Publishing Co., Easton, Pa., 1980). In general, these methods include the step of bringing the compound of formula (I) or salt thereof into association with a pharmaceutically acceptable excipient and/or one or more other additional excipients, and then, if necessary and/or desirable, shaping and/or packaging the product into a desired single dosage form.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the esthetic qualities of the tablets and make them more acceptable to the patient.

Suitable liquid excipients for the preparation of liquid capsule dosage preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added.

The preceding formulations are demonstrative only, and in no way limit the formulations comprising an active compound of the current embodiments. One of skill in the art could recognize and produce additional formulations by methods known in the art. It is an aspect of the present invention that these additional formulations are within the scope of this invention.

WORKING EXAMPLES

Those skilled in the art will recognize that there are a variety of methods available to synthesize molecules represented in the claims. One general strategy is outlined herein, but is in no way meant to limit the scope of the claims.

Figure 1 Structure of the archetypal tocopheryl-DNJ 1 molecule showing the elements (1)

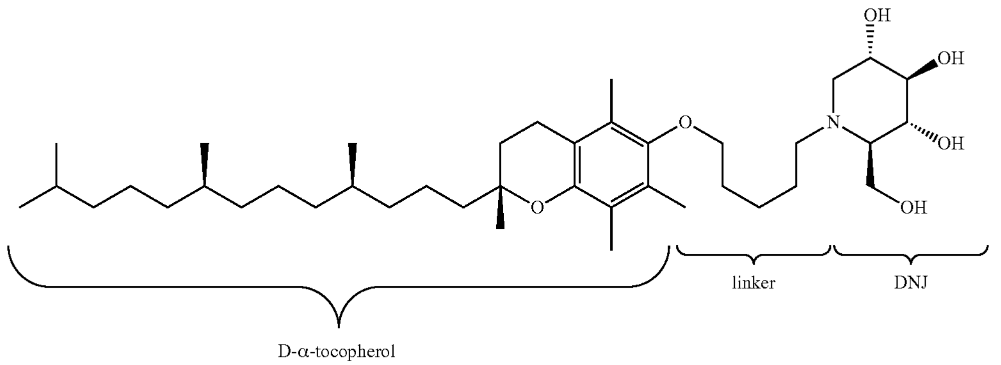

The synthesis of the archetypal tocopheryl-DNJ 1 molecule as shown in FIG. 1, was carried out following the scheme outlined in Scheme 1. Starting from 1,5-pentanediol, a monobenzylation in the presence of silver(I) oxide provides hydroxyether. Subsequent oxidation with Dess-Martin periodinane oxidizes the free alcohol yielding aldehyde. The fully protected compound was obtained from the later compound through treatment with acidic ethylene glycol in refluxing benzene. In order to prepare the aldehyde to be coupled with tocopherol, the protected primary alcohol was first revealed with hydrogenolysis ($H_2$, Pd/C), followed by conversion into a suitable leaving group by treatment with triethylamine ($Et_3N$) and p-toluenesulfonylchloride (TsCl). d-α-tocopherol was irreversibly deprotonated with sodium hydride, then exposed to the tosylate to give modified tocopherol. Hydrolysis of the protective acetal unveiled the aldehyde. 2,3,4,6-tetra-O-benzyl DNJ A (prepared according to Wennekes et al. 2008) and the aldehyde were combined under reductive amination conditions ($H_2$, Pd/C) to give the fully protected Top-DNJ, which, after global deprotection, provided the desired iminosugar 1.

Scheme 1. Chemical synthesis of tocopheryl-deoxynojirimycin (Top-DNJ)

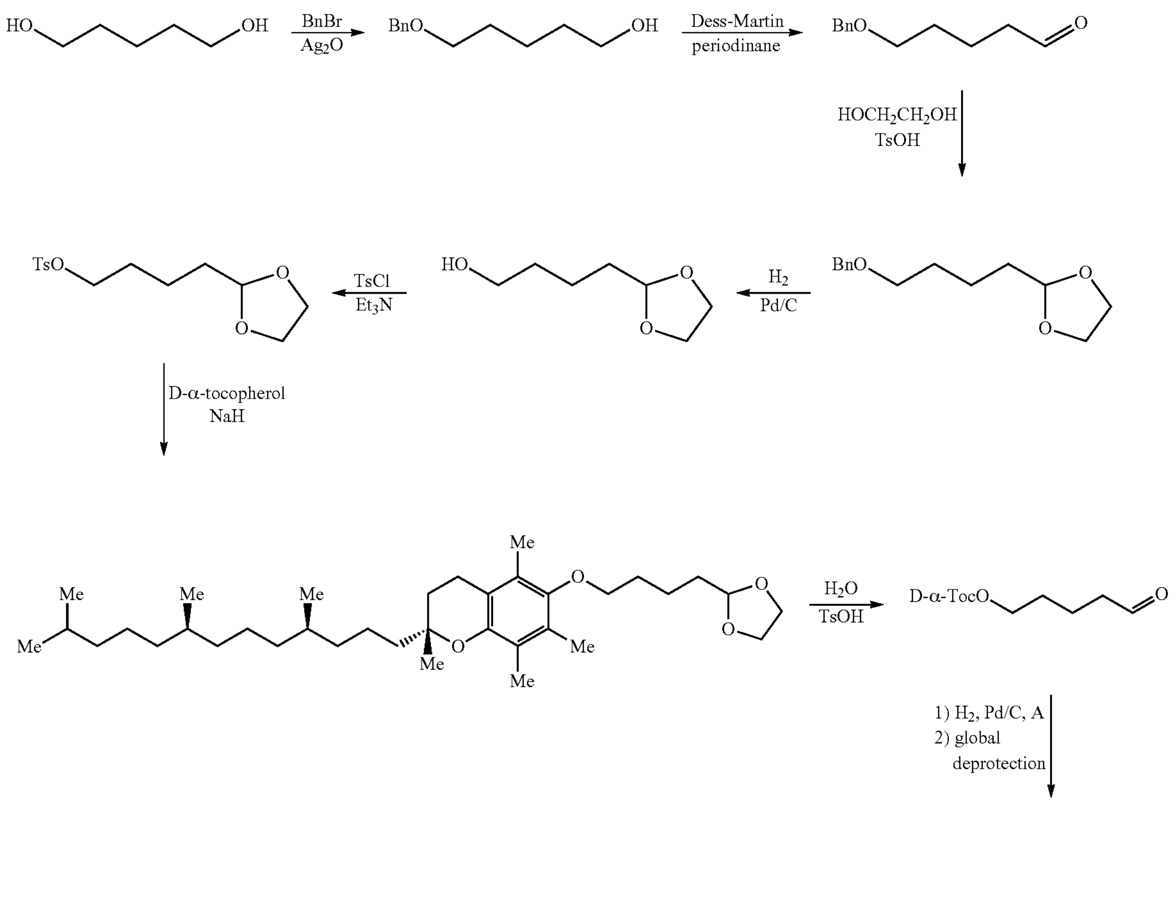

-continued

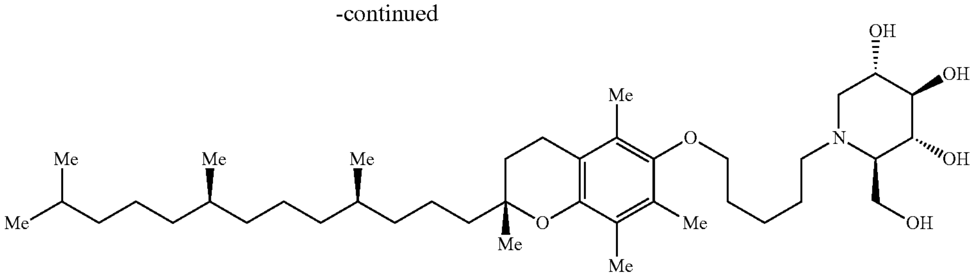

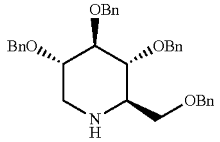

= A

Characterization data for archetypal Top-DNJ 1: $^{1}$H-Nuclear Magnetic Resonance spectrum ($^{1}$H NMR) (500 MHz, $CD_3OD$) δ=3.88 (ddd, J=14.8, 12.1, 2.7 Hz, 2H), 3.63 (t, J=6.3 Hz, 2H), 3.50 (ddd, J=10.3, 9.2, 4.8 Hz, 1H), 3.38 (t, J=9.3 Hz, 1H), 3.16 (t, J=9.1 Hz, 1H), 3.04 (dd, J=11.2, 4.8 Hz, 1H), 2.89, (ddd, J=13.4, 9.3, 6.6 Hz, 1H), 2.72-2.61 (m, 1H), 2.57 (t, J=6.8 Hz, 2H), 2.25 (t, J=10.9 Hz, 1H), 2.20 (br d, J=9.5 Hz, 1H), 2.13 (s, 3H), 2.09 (s, 3H), 2.04 (s, 3H), 1.87-1.67 (m, 4H), 1.67-1.01 (m, 25H), 1.21 (s, 3H), 0.93-0.79 (m, 12H) ppm; $^{13}$C-Nuclear Magnetic Resonance spectrum ($^{13}$C NMR) (125 MHz, $CD_3OD$) δ=149.5, 148.9, 128.5, 126.7, 123.7, 118.7, 111.4, 80.4, 75.7, 73.9, 71.9, 70.6, 67.4, 59.3, 57.6, 53.8, 40.63, 40.55, 38.5, 38.4, 38.3, 33.9, 33.7, 32.8, 31.2, 29.1, 25.9, 25.4, 25.33, 25.25, 24.3, 23.2, 23.1, 22.0, 21.6, 20.3, 13.1, 12.2, 12.1 ppm; High Resolution Mass Spectrum (HRMS) (Electrospray Ionization [ESI], Positive mode [+ve]) m/z: 662.5349 ([M+H]$^{+}$); $C_{40}H_{72}NO_6$ requires 662.5354.

Step 1. 5-(benzyloxy)pentan-1-ol 1,5-pentanediol (2.10 mL, 20.0 mmol, 1.0 equiv.) was dissolved in $CH_2Cl_2$ (100 mL). $Ag_2O$ (6.95 g, 30.0 mmol, 1.5 equiv.) and benzyl bromide (2.62 mL, 22.0 mmol, 1.1 equiv.) were added to the solution sequentially. The flask was wrapped with aluminium foil, and the solution was stirred at room temperature for 18 h. The solution was filtered through a pad of celite, eluting with $CH_2Cl_2$, and concentrated under reduced pressure. The residue was purified by flash column chromatography (silica gel, Ethyl Acetate (EtOAc): petroleum ether (pet ether)=3:17 to 1:1) to give the alcohol as a colorless oil. $^{1}$H NMR (500 MHz, $CDCl_3$) δ=7.37-7.26 (m, 5H), 4.50 (s, 2H), 3.64 (t, J=6.5 Hz, 2H), 3.49 (t, J=6.5 Hz, 2H), 1.70-1.63 (m, 2H), 1.62-1.55 (m, 2H), 1.50-1.42 (m, 2H), 1.34 (br s, 1H) ppm; $^{13}$C NMR (125 MHz, $CDCl_3$) δ=138.8, 128.6, 127.8, 127.7, 73.2, 70.5, 63.1, 32.8, 29.7, 22.7 ppm; Low Resolution Mass Spectrometry (LRMS) (ESI+ve) m/z: 217 (M+Na$^{+}$).

Procedure based on Bouzide and Sauvé, 1997.

Step 2. 5-(benzyloxy)pentanal

The alcohol obtained in Step 1 (20.0 mmol) was dissolved in $CH_2Cl_2$ (100 mL). Dess-Martin periodinane (8.70 g, 20.5 mmol, 1 equiv.) was added, and the resulting solution stirred at room temperature for 18 h. The reaction mixture was then diluted with sat. aq. $NaHCO_3$ (50 mL) and sat. aq. $NaS_2O_3$ (50 mL). The layers were separated, and the aqueous layer extracted with $CH_2Cl_2$ (2×100 mL. The combined organic layers were washed with sat. aq. $NaHCO_3$ (100 mL) and brine (2×100 mL), dried ($MgSO_4$), filtered, and concentrated under reduced pressure. The residue was purified by flash column chromatography (silica gel, EtOAc:pet ether=1:2 to 2:3) to give the resulting aldehyde (2.85 g, 14.8 mmol, 75% yield from the alcohol) as a colorless oil. $^{1}$H NMR (500 MHz, $CDCl_3$) δ=9.76 (t, J=1.7 Hz, 1H), 7.37-7.26 (m, 5H), 4.50 (s, 2H), 3.49 (t, J=6.2 Hz, 2H), 2.46 (td, J=7.2, 1.8 Hz, 2H), 1.79-1.71 (m, 2H), 1.70-1.61 (m, 2H) ppm; $^{13}$C NMR (125 MHz, $CDCl_3$) δ=202.6, 138.7, 128.6, 127.84, 127.79, 73.2, 70.0, 43.8, 29.4, 19.2 ppm; LRMS (ESI+ve): 215 (M+Na$^{+}$).

Step 3. 2-(4-(benzyloxy)butyl)-1,3-dioxolane

The aldehyde resulting from Step 2 (2.85 g, 14.8 mmol, 1.0 equiv) was dissolved in benzene (130 mL). Ethylene glycol (1.1 mL, 19.7 mmol, 1.33 equiv.) and p-toluenesulphonic acid (catalytic) were added. The solution was heated at reflux with a Dean-Stark apparatus for 12 h. The solution was then cooled to room temperature and diluted with sat. aq. $NaHCO_3$ (100 mL) and $CH_2Cl_2$ (300 mL). The layers were separated, and the aqueous layer was extracted with $CH_2Cl_2$ (2×100 mL). The combined organic layers were then dried ($Na_2SO_4$), filtered and concentrated under reduced pressure. The residue was purified by flash column chromatography (silica gel, EtOAc:pet ether=1:9 to 3:17) to give the resulting acetal (2.49 g, 10.5 mmol, 71% yield) as colorless oil. $^{1}$H NMR (500 MHz, $CDCl_3$) δ=7.37-7.26 (m, 5H), 4.86 (t, J=4.8 Hz, 1H), 4.50 (s, 2H), 4.00-3.92 (m, 2H), 3.88-3.81 (m, 2H), 3.48 (t, J=6.6 Hz, 2H), 1.72-1.64 (m, 4H), 1.57-1.48 (m, 2H) ppm; $^{13}$C NMR (125 MHz, $CDCl_3$) δ=138.9, 128.5, 127.8, 127.7, 104.8, 104.7, 73.1, 70.5, 65.1, 33.9, 29.9, 21.0 ppm; LRMS (ESI+ve): 259 (M+Na$^{+}$).

Step 4. 4-(1,3-dioxolan-2-yl)butan-1-ol

Benzyl ether of step 3 (2.00 g, 8.46 mmol, 1.0 equiv) was dissolved under argon in 1,4-dioxane (20 mL). Pd/C (10% Pd, 50 mg, 2.5 weight-%) was added. The mixture was purged with argon, and subsequently with hydrogen. The mixture was stirred at room temperature for 16 h. The solution was filtered (GF/A glass microfiber) and concentrated under reduced pressure to give the resulting alcohol (1.24 g, 8.46 mmol, 100%) as clear, colourless oil which was used in the next step without further purification. $^{1}$H NMR (500 MHz, $CDCl_3$) δ=4.86 (t, J=4.7 Hz, 1H), 4.00-3.91 (m, 2H), 3.90-

3.80 (m, 2H), 3.65 (t, J=6.5 Hz, 2H), 1.74-1.66 (m, 2H), 1.66-1.58 (m, 2H), 1.56-1.46 (m, 2H), 1.40 (br s, 1H) ppm.

Step 5. 4-(1,3-dioxolan-2-yl)butyl 4-methylbenzenesulfonate

To a stirred solution of the alcohol of step 4 (0.50 g, 3.4 mmol, 1.0 equiv.) in $CH_2Cl_2$ (50 mL) at room temperature was added triethylamine (0.62 mL, 4.4 mmol, 1.3 equiv.) followed by p-toluenesulfonylchloride (TsCl, 0.71 g, 3.7 mmol, 1.1 equiv.) and 4-dimethylaminopyridine (50 mg, 0.4 mmol, 0.1 equiv.). The resulting mixture was stirred at that temperature for 8 h. The mixture was diluted with $CH_2Cl_2$ (100 mL) washed with sat. aq. $NaHCO_3$ (100 mL) and brine (2×100 mL), dried ($MgSO_4$), filtered, and concentrated under reduced pressure. While concentrating, the temperature was maintained below 40° C., as the compound had been reported as unstable above this temperature (Wennekes et al. 2008). Due to this instability, the compound was used in the next step crude. $^1$H NMR (500 MHz, $CDCl_3$) δ=7.79 (d, J=8.3 Hz, 2H), 7.34 (d, J=8.4 Hz, 2H), 4.80 (t, J=4.6 Hz, 1H), 4.03 (t, J=6.5 Hz, 2H), 3.96-3.88 (m, 2H), 3.87-3.78 (m, 2H), 2.45 (s, 3H), 1.75-1.65 (m, 2H), 1.65-1.57 (m, 2H), 1.50-1.41 (m, 2H) ppm; $^{13}$C NMR (125 MHz, $CDCl_3$) δ=144.9, 133.5, 130.0, 128.1, 104.4, 70.6, 65.1, 33.3, 29.0, 20.1, 14.4 ppm.

Step 6. (R)-6-(4-(1,3-dioxolan-2-yl)butoxy)-2,5,7,8-tetramethyl-2-((4R,8R)-4,8,12-trimethyltridecyl) chroman To a stirred solution of (+)-α-tocopherol (1.54 g, 3.6 mmol, 1.1 equiv.) in N,N-dimethylformamide (DMF, 30 mL) at 0° C. (ice/water bath) was added NaH (60% in mineral oil, 0.30 g, 7.5 mmol, 2.2 equiv.) in a single portion. After hydrogen gas was no longer being visibly evolved, the cooling bath was removed, and the mixture stirred at room temperature for 1 h. A solution of tosylated compound of Step 5 (crude from previous step, assumed 3.4 mmol, 1.0 equiv) in DMF (10 mL) was added to the reaction mixture at room temperature. The mixture was stirred at 80° C. for 20 h. Solvent was removed by coevaporation with PhMe (3×50 mL). The residue was taken up in EtOAc (250 mL). The solution was then washed with sat. aq. $NaHCO_3$ (50 mL) and brine (50 mL). The combined aqueous fractions were extracted with EtOAc (2×50 mL). The combined organic fractions were then dried ($MgSO_4$), filtered, and concentrated under reduced pressure. The residue was purified by flash column chromatography (silica gel, pet ether to EtOAc:pet ether=1:9) to give the resulting compound (1.65 g, 3.0 mmol, 86% yield) as colorless oil. XX: $^1$H NMR (500 MHz, $CDCl_3$) δ=4.93 (t, J=4.7 Hz, 1H), 4.05-3.94 (m, 2H), 3.92-3.84 (m, 2H), 3.68 (t, J=6.6 Hz, 2H), 2.60 (t, J=6.9 Hz, 2H), 2.20 (s, 3H), 2.16 (s, 3H), 2.12 (s, 3H), 1.93-1.05 (m, 29H), 1.27 (s, 3H), 0.97-0.83 (m, 12H) ppm; $^{13}$C NMR (125 MHz, $CDCl_3$) δ=148.6, 147.8, 127.9, 125.9, 122.9, 117.6, 104.7, 74.8, 72.9, 65.0, 40.3, 39.6, 37.67, 37.65, 37.6, 37.5, 34.1, 33.0, 32.9, 31.5, 30.4, 28.2, 25.0, 24.6, 24.1, 22.9, 22.8, 21.2, 21.0, 20.8, 19.94, 19.85, 12.9, 12.03, 11.9 ppm; HRMS (ESI+ve) m/z: 559.4719 ([M+H]$^+$); $C_{36}H_{63}O_4$ requires 559.4721.

Step 7. 5-(((R)-2,5,7,8-tetramethyl-2-((4R,8R)-4,8,12-trimethyltridecyl)chroman-6-yl)oxy)pentanal To a stirred solution of the compound of Step 6 (521.1 mg, 0.93 mmol, 1.0 equiv.) in 1,4-dioxane (8 mL) at room temperature was added $H_2O$ (1 mL), followed by addition of $TsOH.H_2O$ (0.40 g, 2.1 mmol, 2.2 equiv.) in a single portion. The mixture was stirred at 90° C. Over the next 2 h, $H_2O$ (2 mL) was slowly added. The mixture was then stirred at 90° C. for a further 3 h. The reaction mixture was quenched with sat. aq. $NaHCO_3$ (15 mL) and then extracted with EtOAc (3×20 mL). The combined organic fractions were then dried ($MgSO_4$), filtered, and concentrated under reduced pressure. The residue was purified by flash column chromatography (silica gel, EtOAc:pet ether=1:19 to 6.5:93.5) to give the (408.5 mg, 0.79 mmol, 85% yield) as colorless oil. XX: $^1$H NMR (500 MHz, $CDCl_3$) δ=9.83 (t, J=1.6 Hz, 1H), 3.68 (t, J=6.1 Hz, 2H), 2.65-2.50 (m, 4H), 2.19 (s, 3H), 2.14 (s, 3H), 2.11 (s, 3H), 1.98-1.72 (m, 6H), 1.72-1.03 (m, 21H), 1.26 (s, 3H), 0.96-0.82 (m, 12H) ppm; $^{13}$C NMR (125 MHz, $CDCl_3$) δ=202.3, 148.4, 147.9, 127.9, 125.8, 123.0, 117.7, 74.9, 72.5, 44.0, 40.3, 39.6, 37.68, 37.65, 37.6, 37.5, 33.0, 32.9, 31.5, 30.0, 28.2, 25.0, 24.6, 24.1, 22.9, 22.8, 21.2, 20.9, 19.94, 19.86, 19.3, 12.9, 12.04, 11.96 ppm; HRMS (ESI+ve) m/z: 537.4268 ([M+Na]$^+$); $C_{34}H_{58}NaO_3$ requires 537.4278.

Step 8. 2,3,4,6-tetra-O-benzyl Top-DNJ XX'

To a stirred solution of 2,3,4,6-tetra-O-benzyldeoxynojirimycin (prepared according to Wennekes et al. 2008, 277.0 mg, 0.53 mmol, 1.0 equiv) and the compound of Step 7 (408.5 mg, 0.79 mmol, 1.5 equiv) in ethanol (3 mL) at room temperature was added acetic acid (glacial, 0.3 mL), followed by addition of Pd/C (10% Pd, 30 mg, 10 weight-%) in a single portion. The mixture was purged with argon, and subsequently with hydrogen. The mixture was stirred under hydrogen balloon at 60° C. After 12 h, a further portion of Pd/C (10% Pd, 30 mg, 10 weight-%) was added at room temperature. The reaction mixture was then stirred at 60° C. for a further 36 h. The solution was filtered (GF/A glass microfiber) and concentrated under reduced pressure to give protected 2,3,4,6-tetra-O-benzyl Top-DNJ as clear, colourless oil which was used in the next step without further purification. HRMS (ESI+ve) m/z: 1022.7260 ([M+H]$^+$); $C_{68}H_{96}NO_6$ requires 1022.7232.

Step 9. Top-DNJ of FIG. 1

To a stirred solution of 3,4,6-tetra-O-benzyl Top-DNJ (crude from previous step, assumed 0.78 mmol, 1.0 equiv) in 1:1 methanol:ethanol (50 mL) at room temperature were added cyclohexene (0.8 mL, 7.8 mmol, 10. equiv), ammonium formate (0.50 g, 7.8 mmol, 10. equiv), Pd/C (10% Pd, 0.2 g), and $Pd(OH)_2$ (0.2 g). The mixture was purged with argon, and stirred at reflux for 24 h. Further portions of cyclohexene (0.8 mL, 7.8 mmol, 10. equiv) and ammonium formate (0.50 g, 7.8 mmol, 10. equiv) were added and the reaction mixture stirred at reflux for a further 48 h. The solution was filtered (GF/A glass microfiber), washing the catalyst sequentially with ethanol, methanol, $H_2O$, methanol and ethanol. The combined filtrates were concentrated under reduced pressure. The crude residue was purified by flash column chromatography (silica gel, EtOAc:methanol=19:1 to 17:3) to give the product as colorless foam. $^1$H NMR (500 MHz, $CD_3OD$) δ=3.88 (ddd, J=14.8, 12.1, 2.7 Hz, 2H), 3.63 (t, J=6.3 Hz, 2H), 3.50 (ddd, J=10.3, 9.2, 4.8 Hz, 1H), 3.38 (t, J=9.3 Hz, 1H), 3.16 (t, J=9.1 Hz, 1H), 3.04 (dd, J=11.2, 4.8 Hz, 1H), 2.89, (ddd, J=13.4, 9.3, 6.6 Hz, 1H), 2.72-2.61 (m, 1H), 2.57 (t, J=6.8 Hz, 2H), 2.25 (t, J=10.9 Hz, 1H), 2.20 (br d, J=9.5 Hz, 1H), 2.13 (s, 3H), 2.09 (s, 3H), 2.04 (s, 3H), 1.87-1.67 (m, 4H), 1.67-1.01 (m, 25H), 1.21 (s, 3H), 0.93-0.79 (m, 12H) ppm; $^{13}$C NMR (125 MHz, $CD_3OD$) δ=149.5, 148.9, 128.5, 126.7, 123.7, 118.7, 111.4, 80.4, 75.7, 73.9, 71.9, 70.6, 67.4, 59.3, 57.6, 53.8, 40.63, 40.55, 38.5, 38.4, 38.3, 33.9, 33.7, 32.8, 31.2, 29.1, 25.9, 25.4, 25.33, 25.25, 24.3, 23.2, 23.1, 22.0, 21.6, 20.3, 13.1, 12.2, 12.1 ppm; HRMS (ESI+ve) m/z: 662.5349 ([M+H]$^+$); $C_{40}H_{72}NO_6$ requires 662.5354.

What is claimed is:

1. A compound having formula I:

(I)

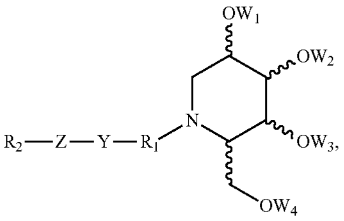

wherein:

$R_1$ is $C_2$-$C_6$ alkyl or $C_2$-$C_6$ alkyl oxaalkyl group;

Y is O or $CH_2$;

Z is

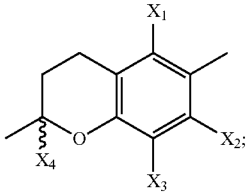

or

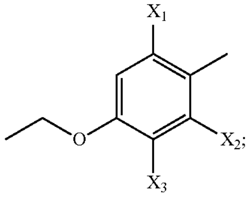

$R_2$ is a) straight or branched $C_{10}$-$C_{16}$ alkyl group, straight or branched $C_{10}$-$C_{16}$ alkylene group or H, when Z is

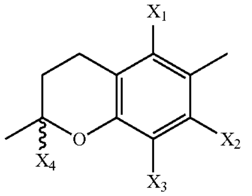

and b) straight or branched $C_{10}$-$C_{20}$ alkyl group or straight or branched $C_{10}$-$C_{20}$ alkylene group, when Z is

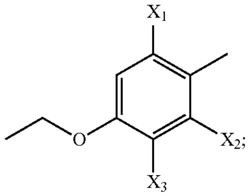

$W_{1-4}$ are each independently selected from H or an alcohol protecting group; and $X_{1-4}$ are each independently selected from H or $C_{1-2}$ alkyl.

2. The compound of claim 1 having formula II (II)

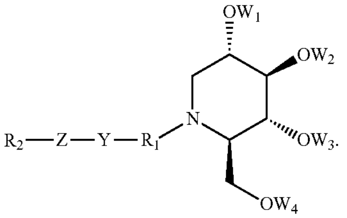

3. The compound of claim 1, wherein $R_1$ is $C_5$ alkyl.

4. The compound of claim 1, wherein —Z—Y— is

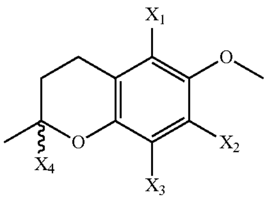

and wherein each of $X_{1-4}$ is independently selected from H or methyl.

5. The compound of claim 4, wherein $X_4$ is methyl and wherein $R_2$—Z—Y— is

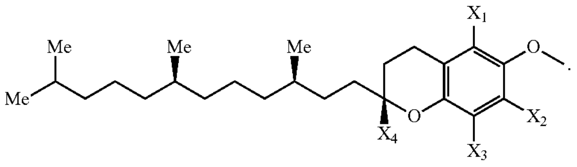

6. The compound of claim 5, wherein $X_{1-4}$ are each methyl and $R_1$ is $C_5$ alkyl.

7. The compound of claim 1, wherein $W_{1-4}$ are each H.

8. The compound of claim 1, wherein $R_2$ is

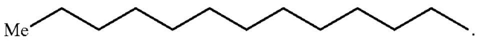

9. A method of making a compound of formula (I)

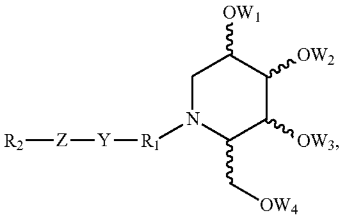

the method comprising:

condensing a compound of formula III (III)

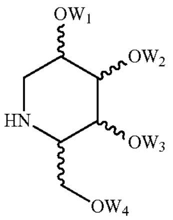

with a compound of formula IV (IV)

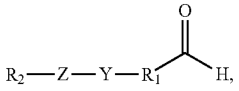

wherein:

$R_1$ is $C_2$-$C_6$ alkyl or $C_{2-6}$ alkyl oxaalkyl group;

Y is O or $CH_2$;

Z is selected from

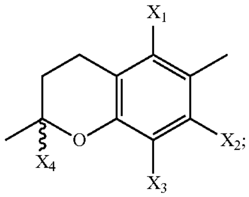

and

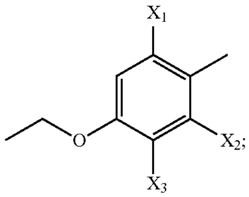

$R_2$ is a) straight or branched $C_{10}$-$C_{16}$ alkyl group, straight or branched $C_{10}$-$C_{16}$ alkylene group or H, when Z is

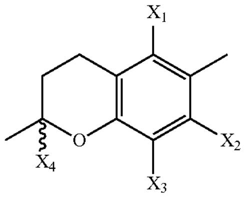

and b) straight or branched $C_{10}$-$C_{20}$ alkyl group or straight or branched $C_{10}$-$C_{20}$ alkylene groups, when Z is

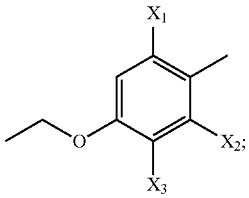

$W_{1-4}$ in the compound of formula I are each independently selected from H or alcohol protecting groups;

$W_{1-4}$ in the compound of formula III are each independently selected from alcohol protecting groups; and $X_{1-4}$ are each independently selected from H or $C_{1-2}$ alkyl.

10. The method of claim 9, wherein the compound of formula I is

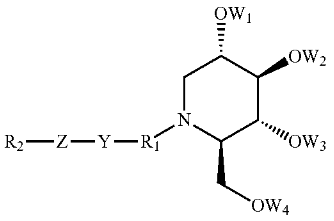

and the compound of formula III is

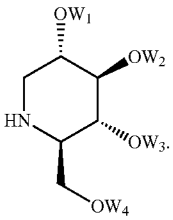

11. The method of claim 9, wherein Y is O.

12. The method of claim 11, further comprising deprotecting compound of formula V (V)

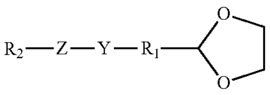

to form the compound of formula IV (IV)

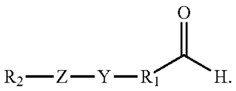

13. The method of claim 12, further comprising reacting $R_2$—Z—OH with

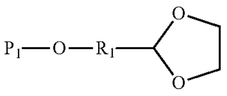

to form the compound of formula V (V)

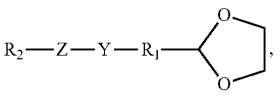

wherein $P_1$ is an alcohol protecting group.

14. The method of claim 11, further comprising converting $R_2$—Z—Y—$R_1$—OH into the compound of formula IV (IV)

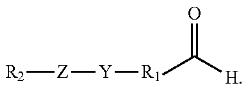

15. The method of claim 14, further comprising deprotecting $R_2$—Z—Y—$R_1$—$OP_2$ to form $R_2$—Z—Y—$R_1$—OH, wherein $P_2$ is an alcohol protecting group.

16. The method of claim 15, further comprising reacting $R_2$—Z—OH with $P_3O$—$R_1$—$OP_2$ to form $R_2$—Z—Y—$R_1$—$OP_2$, wherein $P_3$ is an alcohol protecting group.

17. The method of claim 9, wherein —Z—Y— is

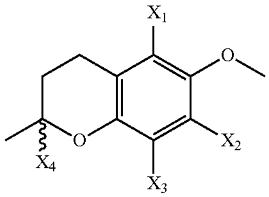

and wherein each of $X_{1-4}$ is independently selected from H or methyl.

* * * * *